(12) United States Patent
Makower et al.

(10) Patent No.: US 8,894,714 B2
(45) Date of Patent: Nov. 25, 2014

(54) UNLINKED IMPLANTABLE KNEE UNLOADING DEVICE

(75) Inventors: Joshua Makower, Los Altos, CA (US); Anton G. Clifford, Mountain View, CA (US); Daniel Pfautz, Hatfield, PA (US); David R. Schiff, Highland Park, NJ (US)

(73) Assignee: Moximed, Inc., Hayward, CA (US)

( * ) Notice: Subject to any disclaimer, the term of this patent is extended or adjusted under 35 U.S.C. 154(b) by 530 days.

(21) Appl. No.: 13/111,744

(22) Filed: May 19, 2011

(65) Prior Publication Data

US 2011/0264216 A1    Oct. 27, 2011

Related U.S. Application Data

(63) Continuation-in-part of application No. 11/743,097, filed on May 1, 2007.

(60) Provisional application No. 61/351,446, filed on Jun. 4, 2010, provisional application No. 61/468,942, filed on Mar. 29, 2011.

(51) Int. Cl.
| | |
|---|---|
| *A61F 2/38* | (2006.01) |
| *A61B 17/68* | (2006.01) |
| *A61B 17/80* | (2006.01) |
| *A61B 17/56* | (2006.01) |

(52) U.S. Cl.
CPC ............. *A61B 17/68* (2013.01); *A61B 17/8061* (2013.01); *A61B 2017/567* (2013.01)
USPC ................... 623/20.21; 623/20.14; 623/20.24; 623/20.22

(58) Field of Classification Search
USPC .......... 623/13.11, 13.15, 17.13, 18.11, 20.12, 623/20.21, 20.24
See application file for complete search history.

(56) References Cited

U.S. PATENT DOCUMENTS

| | | |
|---|---|---|
| 2,632,440 A | 3/1953 | Hauser |
| 2,877,033 A | 3/1959 | Koetke |
| 3,242,922 A | 3/1966 | Thomas |
| 3,648,294 A | 3/1972 | Shahrestani |
| 3,681,786 A | 8/1972 | Lynch |
| 3,779,654 A | 12/1973 | Horne |
| 3,875,594 A | 4/1975 | Swanson |
| 3,902,482 A | 9/1975 | Taylor |

(Continued)

FOREIGN PATENT DOCUMENTS

| | | |
|---|---|---|
| CA | 1205602 | 6/1986 |
| DE | 19855254 | 6/2000 |

(Continued)

OTHER PUBLICATIONS

Orthofix; "Gentle Limb Deformity Correction", website pages, http://www.eight-plate.com/, 2008.

(Continued)

*Primary Examiner* — Corrine M McDermott
*Assistant Examiner* — Joshua Levine
(74) *Attorney, Agent, or Firm* — Cermak Nakajima & McGowan LLP; Adam J. Cermak

(57) ABSTRACT

A system and method for sharing and absorbing energy between body parts. In one particular aspect, the system is an unlinked structure which facilitates absorbing energy between members forming a joint such as between articulating bones.

6 Claims, 23 Drawing Sheets

(56) References Cited

U.S. PATENT DOCUMENTS

| | | | |
|---|---|---|---|
| 3,988,783 A | 11/1976 | Treace |
| 4,054,955 A | 10/1977 | Seppo |
| 4,187,841 A | 2/1980 | Knutson |
| 4,246,660 A | 1/1981 | Wevers |
| 4,308,863 A | 1/1982 | Fischer |
| 4,353,361 A | 10/1982 | Foster |
| 4,501,266 A | 2/1985 | McDaniel |
| 4,570,625 A | 2/1986 | Harris |
| 4,576,158 A | 3/1986 | Boland |
| 4,621,627 A | 11/1986 | Debastiani et al. |
| 4,637,382 A | 1/1987 | Walker |
| 4,696,293 A | 9/1987 | Ciullo |
| 4,759,765 A | 7/1988 | Van Kampen |
| 4,776,851 A | 10/1988 | Bruchman et al. |
| 4,846,842 A | 7/1989 | Connolly et al. |
| 4,863,471 A | 9/1989 | Mansat |
| 4,871,367 A | 10/1989 | Christensen et al. |
| 4,873,967 A | 10/1989 | Sutherland |
| 4,883,486 A | 11/1989 | Kapadia et al. |
| 4,923,471 A | 5/1990 | Morgan |
| 4,942,875 A | 7/1990 | Hlavacek et al. |
| 4,943,053 A | 7/1990 | Smith |
| 4,959,065 A | 9/1990 | Arnett et al. |
| 4,988,349 A | 1/1991 | Pennig |
| 5,002,574 A | 3/1991 | May et al. |
| 5,011,497 A | 4/1991 | Persson et al. |
| 5,019,077 A | 5/1991 | De Bastiani et al. |
| 5,026,372 A | 6/1991 | Sturtzkopf et al. |
| 5,037,426 A | 8/1991 | Goble et al. |
| 5,041,112 A | 8/1991 | Mingozzi et al. |
| 5,100,403 A | 3/1992 | Hotchkiss et al. |
| 5,103,811 A | 4/1992 | Crupi |
| 5,121,742 A | 6/1992 | Engen |
| 5,152,280 A | 10/1992 | Danieli |
| 5,282,867 A | 2/1994 | Mikhail |
| 5,314,478 A | 5/1994 | Oka et al. |
| 5,318,567 A | 6/1994 | Vichard |
| 5,352,190 A | 10/1994 | Fischer |
| 5,375,823 A | 12/1994 | Navas |
| 5,405,347 A | 4/1995 | Lee et al. |
| 5,415,661 A | 5/1995 | Holmes |
| 5,443,518 A | 8/1995 | Insall |
| 5,456,722 A | 10/1995 | McLeod et al. |
| 5,540,688 A | 7/1996 | Navas |
| 5,564,437 A | 10/1996 | Bainville et al. |
| 5,575,819 A | 11/1996 | Amis |
| 5,578,038 A | 11/1996 | Slocum |
| 5,601,553 A | 2/1997 | Trebling |
| 5,624,440 A | 4/1997 | Huebner |
| 5,662,648 A | 9/1997 | Faccioli et al. |
| 5,662,650 A | 9/1997 | Bailey et al. |
| 5,681,313 A | 10/1997 | Diez |
| 5,695,496 A | 12/1997 | Orsak |
| 5,716,357 A | 2/1998 | Rogozinski |
| 5,803,924 A | 9/1998 | Oni et al. |
| 5,830,216 A | 11/1998 | Insall et al. |
| 5,873,843 A | 2/1999 | Draper |
| 5,928,234 A | 7/1999 | Manspeizer |
| 5,976,125 A | 11/1999 | Graham |
| 5,976,136 A | 11/1999 | Bailey |
| 6,036,691 A | 3/2000 | Richardson |
| 6,080,196 A | 6/2000 | Bertin |
| 6,113,637 A | 9/2000 | Gill et al. |
| 6,132,433 A | 10/2000 | Whelan |
| 6,139,550 A | 10/2000 | Michelson |
| 6,162,223 A | 12/2000 | Orsak et al. |
| 6,176,860 B1 | 1/2001 | Howard |
| 6,193,225 B1 | 2/2001 | Watanabe |
| 6,205,411 B1 | 3/2001 | DiGioia et al. |
| 6,206,880 B1 | 3/2001 | Karladani |
| 6,264,696 B1 | 7/2001 | Reigner et al. |
| 6,277,124 B1 | 8/2001 | Haag |
| 6,315,852 B1 | 11/2001 | Magrini et al. |
| 6,355,037 B1 | 3/2002 | Crosslin et al. |
| 6,364,881 B1 | 4/2002 | Apgar et al. |
| 6,395,005 B1 | 5/2002 | Lovell |
| 6,409,729 B1 | 6/2002 | Martinelli et al. |
| 6,482,232 B1 | 11/2002 | Boucher et al. |
| 6,494,914 B2 | 12/2002 | Brown et al. |
| 6,527,733 B1 | 3/2003 | Ceriani et al. |
| 6,540,708 B1 | 4/2003 | Manspeizer |
| 6,572,653 B1 | 6/2003 | Simonson |
| 6,599,322 B1 | 7/2003 | Amrich et al. |
| 6,620,332 B2 | 9/2003 | Amrich |
| 6,623,486 B1 | 9/2003 | Weaver et al. |
| 6,663,631 B2 | 12/2003 | Kuntz |
| 6,692,497 B1 | 2/2004 | Tormala et al. |
| 6,692,498 B1 | 2/2004 | Niiranen et al. |
| 6,726,684 B1 | 4/2004 | Woloszko |
| 6,752,831 B2 | 6/2004 | Sybert et al. |
| 6,849,076 B2 | 2/2005 | Blunn et al. |
| 6,884,242 B2 | 4/2005 | LeHuec et al. |
| 6,966,910 B2 | 11/2005 | Ritland |
| 6,972,020 B1 | 12/2005 | Grayson et al. |
| 6,997,940 B2 | 2/2006 | Bonutti |
| 7,018,418 B2 | 3/2006 | Amrich et al. |
| 7,029,475 B2 | 4/2006 | Pajabi |
| 7,097,662 B2 | 8/2006 | Evans et al. |
| 7,104,996 B2 | 9/2006 | Bonutti |
| 7,128,744 B2 | 10/2006 | Weaver et al. |
| 7,141,073 B2 | 11/2006 | May et al. |
| 7,153,327 B1 | 12/2006 | Metzger |
| 7,188,626 B2 | 3/2007 | Foley et al. |
| 7,201,728 B2 | 4/2007 | Sterling |
| 7,235,077 B1 | 6/2007 | Wang et al. |
| 7,235,102 B2 | 6/2007 | Ferree et al. |
| 7,238,203 B2 | 7/2007 | Bagga et al. |
| 7,241,298 B2 | 7/2007 | Nemec et al. |
| 7,247,157 B2 | 7/2007 | Prager et al. |
| 7,252,670 B2 | 8/2007 | Morrison et al. |
| 7,261,739 B2 | 8/2007 | Ralph et al. |
| 7,273,481 B2 | 9/2007 | Lombardo et al. |
| 7,276,070 B2 | 10/2007 | Muckter |
| 7,282,065 B2 | 10/2007 | Kirschman |
| 7,285,134 B2 | 10/2007 | Berry et al. |
| 7,288,094 B2 | 10/2007 | Lindemann et al. |
| 7,288,095 B2 | 10/2007 | Baynham et al. |
| 7,291,150 B2 | 11/2007 | Graf |
| 7,306,605 B2 | 12/2007 | Ross |
| 7,322,983 B2 | 1/2008 | Harris |
| 7,322,984 B2 | 1/2008 | Doubler et al. |
| 7,341,589 B2 | 3/2008 | Weaver et al. |
| 7,361,196 B2 | 4/2008 | Fallin et al. |
| 2001/0020143 A1 | 9/2001 | Stark et al. |
| 2002/0095154 A1 | 7/2002 | Atkinson et al. |
| 2002/0107570 A1 | 8/2002 | Sybert et al. |
| 2002/0151903 A1 | 10/2002 | Takei et al. |
| 2002/0151978 A1 | 10/2002 | Zacouto et al. |
| 2003/0149436 A1 | 8/2003 | McDowell |
| 2003/0216809 A1 | 11/2003 | Ferguson |
| 2004/0019382 A1 | 1/2004 | Amirouche et al. |
| 2004/0039395 A1 | 2/2004 | Coon et al. |
| 2004/0044295 A1 | 3/2004 | Reinert et al. |
| 2004/0078042 A1 | 4/2004 | Masini |
| 2004/0152970 A1 | 8/2004 | Hunter et al. |
| 2004/0260302 A1* | 12/2004 | Manspeizer .................... 606/90 |
| 2004/0267179 A1 | 12/2004 | Leman |
| 2005/0049708 A1 | 3/2005 | Atkinson et al. |
| 2005/0085815 A1 | 4/2005 | Harms et al. |
| 2005/0101966 A1 | 5/2005 | Lavallee |
| 2005/0113927 A1 | 5/2005 | Malek |
| 2005/0119744 A1 | 6/2005 | Buskirk et al. |
| 2005/0154390 A1 | 7/2005 | Biedermann et al. |
| 2005/0192674 A1 | 9/2005 | Ferree |
| 2005/0197569 A1 | 9/2005 | McCombs |
| 2005/0251065 A1 | 11/2005 | Henning et al. |
| 2005/0251080 A1 | 11/2005 | Hyde, Jr. |
| 2005/0261680 A1 | 11/2005 | Draper |
| 2006/0064169 A1* | 3/2006 | Ferree .................... 623/17.12 |
| 2006/0178744 A1 | 8/2006 | de Villiers et al. |
| 2006/0189983 A1 | 8/2006 | Fallin et al. |
| 2006/0282023 A1 | 12/2006 | Leitner |
| 2007/0043356 A1 | 2/2007 | Timm et al. |
| 2007/0083272 A1 | 4/2007 | Van De Veen et al. |

(56) References Cited

U.S. PATENT DOCUMENTS

| | | | |
|---|---|---|---|
| 2007/0088442 A1 | 4/2007 | Cima et al. |
| 2007/0106299 A1 | 5/2007 | Manspeizer |
| 2007/0161993 A1 | 7/2007 | Lowery et al. |
| 2007/0168033 A1 | 7/2007 | Kim et al. |
| 2007/0168036 A1 | 7/2007 | Ainsworth et al. |
| 2007/0198088 A1 | 8/2007 | Biedermann et al. |
| 2007/0198091 A1 | 8/2007 | Boyer et al. |
| 2007/0244483 A9 | 10/2007 | Winslow et al. |
| 2007/0244488 A1 | 10/2007 | Metzger et al. |
| 2007/0244565 A1 | 10/2007 | Stchur |
| 2007/0288014 A1 | 12/2007 | Shadduck et al. |
| 2008/0015591 A1 | 1/2008 | Castaneda et al. |
| 2008/0015592 A1 | 1/2008 | Long et al. |
| 2008/0015593 A1 | 1/2008 | Pfefferle et al. |
| 2008/0044449 A1 | 2/2008 | McKay |
| 2008/0071373 A1 | 3/2008 | Molz et al. |
| 2008/0071375 A1 | 3/2008 | Carver et al. |
| 2008/0097434 A1 | 4/2008 | Moumene et al. |
| 2008/0097441 A1 | 4/2008 | Hayes et al. |
| 2008/0132954 A1 | 6/2008 | Sekhon et al. |
| 2008/0154378 A1 | 6/2008 | Pelo |
| 2008/0275509 A1 | 11/2008 | Clifford et al. |
| 2008/0275555 A1 | 11/2008 | Makower et al. |
| 2008/0275560 A1 | 11/2008 | Clifford et al. |
| 2008/0275561 A1 | 11/2008 | Clifford et al. |
| 2008/0319512 A1 | 12/2008 | Sherman |
| 2009/0228045 A1 | 9/2009 | Hayes |

FOREIGN PATENT DOCUMENTS

| | | |
|---|---|---|
| EP | 2223406 | 4/1990 |
| EP | 0383419 | 8/1990 |
| EP | 0953317 | 4/1999 |
| EP | 1770302 | 4/2007 |
| EP | 1429675 | 10/2007 |
| EP | 1682020 | 10/2007 |
| EP | 1847228 | 10/2007 |
| EP | 1847229 | 10/2007 |
| EP | 1005290 | 2/2008 |
| EP | 1468655 | 5/2008 |
| GB | 1507953 | 4/1978 |
| GB | 2250919 | 10/1993 |
| JP | 59-131348 | 7/1984 |
| JP | 7-100159 | 4/1995 |
| JP | 2532346 | 4/1995 |
| JP | 2000-503865 | 4/2000 |
| JP | 2001-145647 | 4/2000 |
| JP | 2003-102744 | 5/2001 |
| JP | 2006-280951 | 10/2006 |
| JP | 2007-167318 | 7/2007 |
| JP | 2007-167319 | 7/2007 |
| JP | 2007-170969 | 7/2007 |
| NZ | 533300 | 2/2005 |
| RU | 1769868 | 10/1992 |
| RU | 2085148 | 7/1997 |
| RU | 2217105 | 11/2003 |
| RU | 2241400 | 9/2004 |
| SU | 578063 | 11/1977 |
| SU | 578957 | 11/1977 |
| SU | 1186204 | 10/1985 |
| SU | 1251889 | 8/1986 |
| SU | 1316666 | 6/1987 |
| SU | 1588404 | 8/1990 |
| SU | 1699441 | 12/1991 |
| WO | WO9107137 | 5/1991 |
| WO | WO9406364 | 3/1994 |
| WO | WO9619944 | 7/1996 |
| WO | WO2004019831 | 3/2004 |
| WO | WO2004024037 | 3/2004 |
| WO | WO2007056645 | 5/2005 |
| WO | WO2006045091 | 4/2006 |
| WO | WO2006049993 | 5/2006 |
| WO | WO2006110578 | 10/2006 |
| WO | WO2007090009 | 8/2007 |
| WO | WO2007090015 | 8/2007 |
| WO | WO2007090017 | 8/2007 |
| WO | WO2007106962 | 9/2007 |
| WO | WO2007109132 | 9/2007 |
| WO | WO2007109140 | 9/2007 |
| WO | WO2007109417 | 9/2007 |
| WO | WO2007109436 | 9/2007 |
| WO | WO2007114769 | 10/2007 |
| WO | WO2007117571 | 10/2007 |
| WO | WO2008006098 | 1/2008 |
| WO | WO2009/155542 | 12/2009 |

OTHER PUBLICATIONS

Perry, Clayton R et al.; "Patellar Fixation Protected with a Load-Sharing Cable: A Mechanical and Clinical Study": Journal of Orthopaedic Trauma, 1988, vol. 2, No. 3, pp. 234-240.

Pilliar et al., Bone ingrowth and Stress Shielding with a Porous Surface Coated Fracture Fixation Plate, Journal of Biomedical Materials Research, vol. 13, 799-810 (1979).

Pollo, Fabian E. et al.; "Reduction of Medical Compartment Loads With Valgus Bracing of the Osteoarthritic Knee"; American Journal Sports Medicine, vol. 30, No. 3, 2002; pp. 414-421.

Repicci, John A., M.D. et al. "Minimally invasive unicondylar knee arthroplasty for the treatment of unicompartmental osteoarthritis: an outpatient bypass procedure"; Orthopaedic Clinics of North America, 35 (2004), pp. 201-216.

Sharma, Leena et al.; "The Mechanism of the Effect of Obesity in Knee Osteoarthritis—The Mediating Role of Malalignment"; Arthritis & Rheumatism, vol. 43, No. 3, Mar. 2000, pp. 568-575.

Sharma, Leena, M.D. et al.; "The Role of Knee Alignment in Disease Progression and Functional Decline in Knee Osteoarthritis"; JAMA, Jul. 11, 2001, vol. 286, No. 2, pp. 188-196.

Sommerkamp, G. et al.; "Dynamic external fixation of unstable reatures of the distal part of the radius"; The Journal of Bone and Joint Surgery; 1994, vol. 76-A, No. 8, pp. 1149-1161.

Tencer, Allan F. et al. "Fixation of the Patell (Chap, 9.3)"; in: Biomechanics in Orthopedic Trauma Bone Fracture and Fixation, 1994.

Thakur, A.J.; "Tension Band Wiring"; in; The Elements of Fracture Fixation 1997.

Uchikura, C. et al.; "Comparative study of nonbridging and bridging external fixators for unstable distal radius fractures"; Journal of Orthopaedic Science, 2004, vol. 9, pp. 560-565.

Weisstein, Jason S., M.D. et al.; "Oncologic Approaches to Pediatric Limb Preservation"; Journal of the American Academy of Orthopaedic Surgeons; vol. 13, No. 8, Dec. 2005.

Van Der Esch, M. et al.; "Structural joint changes, malalignment, and laxity in osteoarthritis of the knee"; Scand J. Rheumatol 2005; 34: 298-301.

Wilke, Hans-Joachim et al., "Biomechanical Evaluation of a New Total Posterior-Element Replacement System"; Spine, 2006, vol. 31, No. 24, pp. 2790-2796.

Wilkins, Ross M., M.D. et al.; "The Phenix Expandable Prosthesis"; Clinical Orthopaedics and Related Research, No. 382, pp. 51-58.

Yamamoto, Ei et al.; "Effects of Stress Shielding on the Transverse Mechanical Properties of Rabbit Patellar Tendons"; Journal of Biomechanical Engineering, 2000, vol. 122, pp. 608-614.

Lapinskaya, Valentina Spiridovna, "Treatment of Diseases and Injuries of Hip Joint Using a Method of Distractions", Kuibyshev Medial Institute, 1990.

Larionov d. Yu, et al., "Medical Devices", Scientific and Technical Bimonthly Journal, May-Jun. 2008.

Lapinskaya, V.S., et al., "An Endoapparatus for Restoration of the Hip Joint", Writers Collective, 2008, UDK 615.472.03:616,728.2-089.28.

Nagai, et al., "B109 Mobility Evaluation of Hip-Joint Nonweight-Bearing Device", The Japan Society of Mechanical Engineers No. 02-26.

Tomita, Naohide, "Development of Treatment Devices for Cartilage Regeneration", BME vol. 16, No. 2.

Lentsner, A.A., et al., "Device for Functional Relief of Hip Joint in Cotyloid Cavity Fracture Cases", Ortop Travmatol Protez. Apr. 1990 (4) 44-6.

(56) References Cited

OTHER PUBLICATIONS

Aldegheri, Roberto, M.D. et al.; "Articulated Distraction of the Hip—Conservative Surgery for Arthritis in Young Patients", Clinical Orthopaedics and Related Research, No. 301, pp. 94-101.

Andriacchi, Thomas P., Ph.D. et al. "Methods for evaluating the progression of osteoarthritis"; Journal of Rehabilitation Research and Development, vol. 37, No. 2, Mar./Apr. 2000, pp. 163-170.

Arendt, Elizabeth, M.D.; Anatomy and Malalignment of the Patellofemoral Joint—It's Relation to Patellofemoral Arthrosis; Clinical Orthopaedics and Related Research; 2005, No. 436, pp. 71-75.

Benzel, Edward; "Qualititive Attributes of Spinal Implants"; in: Biomechanics of Spine Stabilization, 1995.

Buckwalter, Joseph A,: "Joint distraction for osteoarthritis"; The Lancet, Department of Orthopaedic Surgery, University of Iowa Hospitals and Clinics, vol. 347, Feb. 3, 1996, pp. 279-280.

Coathup, M.J. et al.; "Osseo-mechanical induction of extro-cortiacal plates with references to their surfact properties and goemoetic designs", Elsevier, Biomaterials 20 (1999) 793-800.

Deie, Masataka, M.D. et al.; "A new Articulated Distraction Arthrosplasty Device for Treatment of the Osteoarthritic Knee Joint: A Preliminary Report"; Arthroscopy: The Journal of Arthoscopic and Related Surgery; vol. 23, No. 8 Aug. 2007: pp. 833-838.

Dienst, M. et al.; "Dynamic external fixation for distal radius fractures"; Clinical Orthopaedics and Related Research, 1997, vol. 338, pp. 160-171.

Gunther, Klaus-Peter, M.D.; "Surgical approaches for osteoarthritis"; Best Practice and Research Clinical Rheumatology, vol. 15, No. 4, pp. 627-643, 2001.

Hall, J. et al.; "Use of a hinged external fixator for elbow instability after severe distal humeral fracture"; Journal of Orthopaedic Trauma, 2000, vol. 14, No. 6 pp. 442-448.

Klein, D. et al.; "Percutaneous treatment of carpal, metacarpal, and phalangeal injuries"; Clinical Orthopaedics and Related Research, 200, vol. 375, pp. 116-125.

Krakauer, J. et al.; "Hinged device for fractures involving the proximal interphalangeal joint"; Clinical Orthopaedics and Related Research, 1996, vol. 327, pp. 29-37.

Lafeber et al., Unloading Joints to Treat Osteoarthritis, Including Joint Distraction, Current Opinion in Rheumatology 2006, 18; 519-525.

Leon, Hariberto Ojeda, M.D. et al.; "Minimally Invasive Selective Osetotomy of the Knee: A New Surgical Technique"; Arthroscopy: The Journal of Arthroscopic and Related Surgery, Vol, 17, No. 5 May-Jun. 2001: pp. 510-516.

Madey, S. et al; Hinged external fixation of the elbow: optimal axis alignment to minimize motion resistance; Journal of Orthopaedic Trauma, 2000, vol. 14, No. 1, pp. 41-47.

Neel, Michael D. M.D. et al.; "Early Multicenter Experience With a Noninvasive Expandable Prosthesis"; Clinical Orthopaedics and Related Research, 2003, No. 415, pp. 72-81.

Neel, Michael D., M.D.; "Repiphysis—Limb Salvage System for the Skeletally Immature"; Wright Medical Techology, Repiphysis Limb Salvage System, 2001, pp. 1-8.

Nockels, Russ P.; "Dynamic Stabilization in the Surgical Management of Painful Lumbar Spinal Disorders"; Spine, 2005, vol. 30, No. 16S, pp. S68-S72.

Orthofix; "Xcaliber Articulated Ankle"; advertising brochure, May 2004.

* cited by examiner

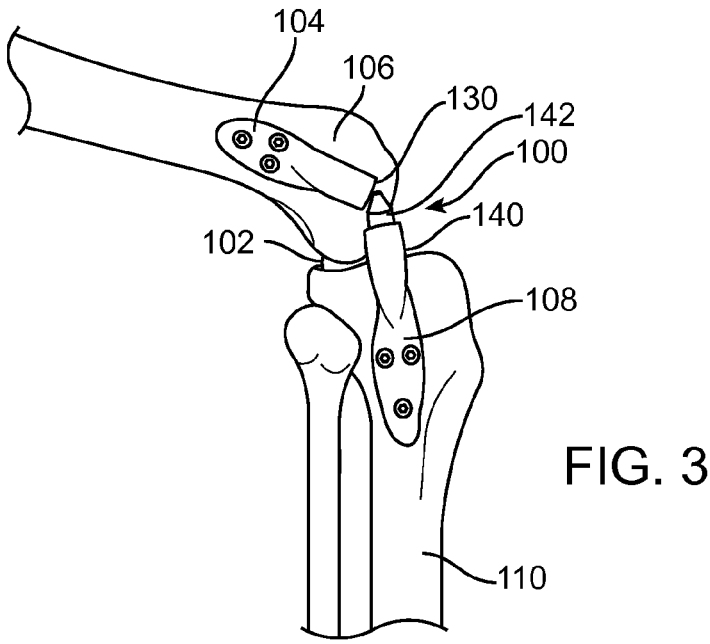
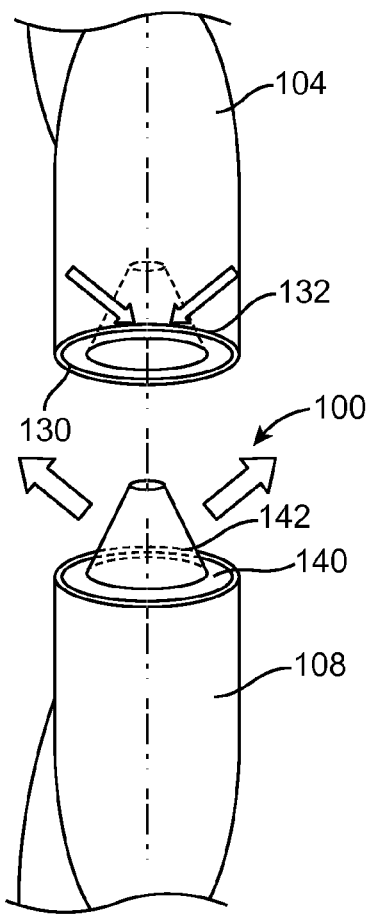
FIG. 4
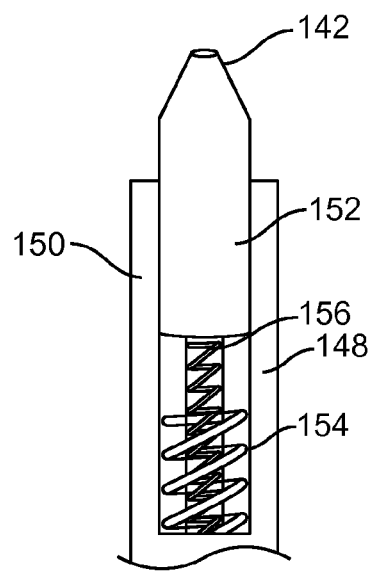
FIG. 5

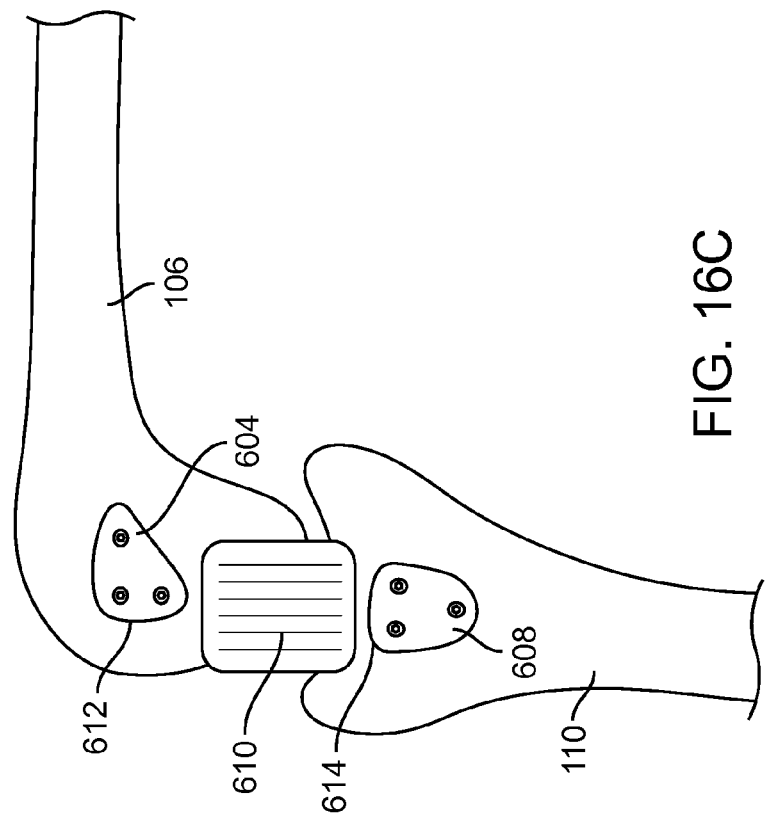
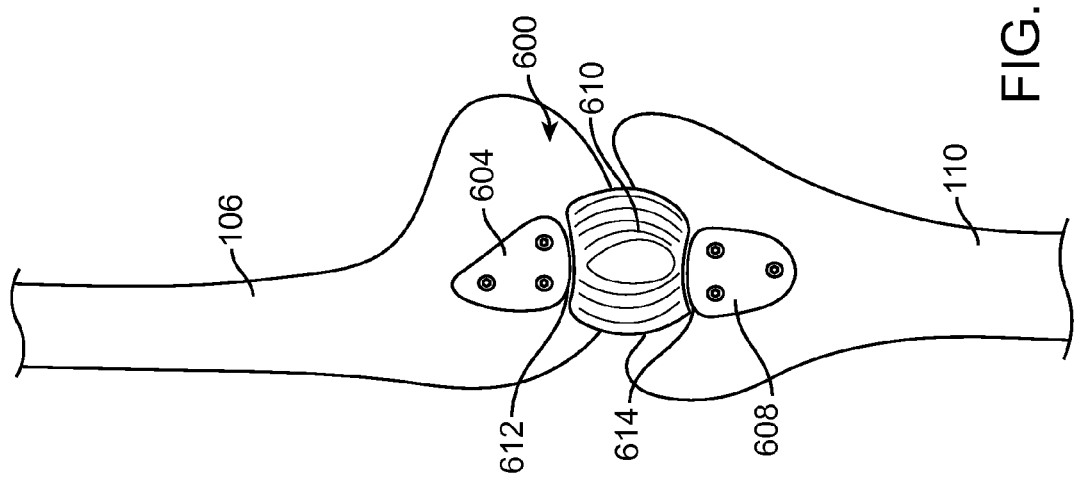

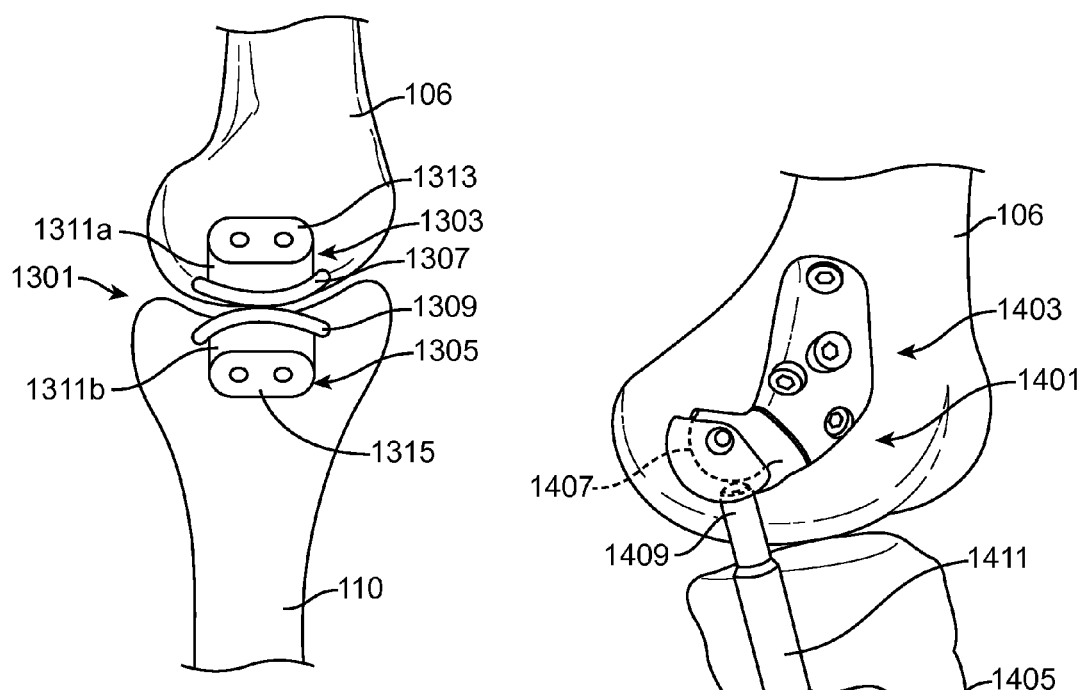
FIG. 26
FIG. 27
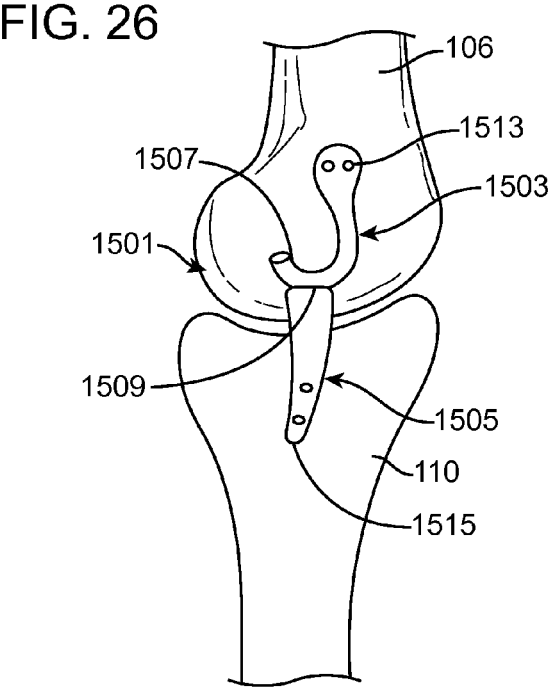
FIG. 28

UNLINKED IMPLANTABLE KNEE UNLOADING DEVICE

CROSS-REFERENCES TO RELATED APPLICATIONS

This application is a continuation-in-part of U.S. application Ser. No. 11/743,097, filed May 1, 2007, and claims the benefit of U.S. Application Ser. No. 61/351,446, filed Jun. 4, 2010 and U.S. Application Ser. No. 61/468,942, filed Mar. 29, 2011, the entire disclosure of which is expressly incorporated herein by reference.

BACKGROUND OF THE INVENTION

Various embodiments disclosed herein are directed to structures for unloading body anatomy, and more particularly, towards approaches to devices for unloading joints.

Joint replacement is one of the most common and successful operations in modern orthopaedic surgery. It consists of replacing painful, arthritic, worn or diseased parts of a joint with artificial surfaces shaped in such a way as to allow joint movement. Osteoarthritis is a common diagnosis leading to joint replacement. Such joint replacement procedures are a last resort treatment as they are highly invasive and require substantial periods of recovery. Total joint replacement, also known as total joint arthroplasty, is a procedure in which all articular surfaces at a joint are replaced. This contrasts with hemiarthroplasty (half arthroplasty) in which only one bone's articular surface at a joint is replaced and unicompartmental arthroplasty in which the articular surfaces of only one of multiple compartments at a joint (such as the surfaces of the thigh and shin bones on just the inner side or just the outer side at the knee) are replaced.

Arthroplasty, as a general term, is an orthopaedic procedure which surgically alters the natural joint in some way. Arthroplasty includes procedures in which the arthritic or dysfunctional joint surface is replaced with something else as well as procedures which are undertaken to reshape or realigning the joint by osteotomy or some other procedure. A previously popular form of arthroplasty was interpositional arthroplasty in which the joint was surgically altered by insertion of some other tissue like skin, muscle or tendon within the articular space to keep inflammatory surfaces apart. Another less popular arthroplasty is excisional arthroplasty in which articular surfaces are removed leaving scar tissue to fill in the gap. Among other types of arthroplasty are resection(al) arthroplasty, resurfacing arthroplasty, mold arthroplasty, cup arthroplasty, silicone replacement arthroplasty, and osteotomy to affect joint alignment or restore or modify joint congruity.

The most common arthroplasty procedures including joint replacement, osteotomy procedures and other procedures in which the joint surfaces are modified are highly invasive procedures and are characterized by relatively long recovery times. When it is successful, arthroplasty results in new joint surfaces which serve the same function in the joint as did the surfaces that were removed. Any chodrocytes (cells that control the creation and maintenance of articular joint surfaces), however, are either removed as part of the arthroplasty, or left to contend with the resulting new joint anatomy and injury. Because of this, none of these currently available therapies are chondro-protective.

A widely-applied type of osteotomy is one in which bones beside the joint are surgically cut and realigned to improve alignment in the joint. A misalignment due to injury or disease in a joint related to the direction of load can result in an imbalance of forces and pain in the affected joint. The goal of osteotomy is to surgically re-align the bones at a joint such as by cutting and reattaching part of one of the bones to change the joint alignment. This realignment relieves pain by equalizing forces across the joint. This can also increase the lifespan of the joint. The surgical realignment of the knee joint by high tibial osteotomy (HTO) (the surgical re-alignment of the upper end of the shin bone (tibia) to address knee malalignment) is an osteotomy procedure done to address osteoarthritis in the knee. When successful, HTO results in a decrease in pain and improved function. However, HTO does not address ligamentous instability—only mechanical alignment. Good early results associated with HTO often deteriorate over time.

Other approaches to treating osteoarthritis involve an analysis of loads which exist at a joint and attempts to correct (generally reduce) these loads. Both cartilage and bone are living tissues that respond and adapt to the loads they experience. Within a nominal range of loading, bone and cartilage remain healthy and viable. If the load falls below the nominal range for extended periods of time, bone and cartilage can become softer and weaker (atrophy). If the load rises above the nominal level for extended periods of time, bone can become stiffer and stronger (hypertrophy). Osteoarthritis or breakdown of cartilage due to wear and tear can also result from overloading. When cartilage breaks down, the bones rub together and cause further damage and pain. Finally, if the load rises too high, then abrupt failure of bone, cartilage and other tissues can result.

The treatment of osteoarthritis and other bone and cartilage conditions is severely hampered when a surgeon is not able to control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there is a need for devices which facilitate the control of load on a joint undergoing treatment or therapy, to thereby enable use of the joint within a healthy loading zone.

Certain other approaches to treating osteoarthritis contemplate external devices such as braces or fixators which attempt to control the motion of the bones at a joint or apply cross-loads at a joint to shift load from one side of the joint to the other. A number of these approaches have had some success in alleviating pain. However, lack of patient compliance and the inability of the devices to facilitate and support the natural motion and function of the diseased joint have been problems with these external braces.

Prior approaches to treating osteoarthritis have also failed to account for all of the basic functions of the various structures of a joint in combination with its unique movement. In addition to addressing the loads and motions at a joint, an ultimately successful approach must also acknowledge the dampening and energy absorption functions of the anatomy. Prior devices designed to reduce the load transferred by the natural joint typically incorporate relatively rigid constructs that are incompressible. Mechanical energy (E) is the action of a force (F) through a distance (s) (i.e., $E=F \times s$). Device constructs which are relatively rigid do not allow substantial energy storage as they do not allow substantial deformations—do not act through substantial distances. For these relatively rigid constructs, energy is transferred rather than stored or absorbed relative to a joint. By contrast, the natural joint is a construct comprised of elements of different compliance characteristics such as bone, cartilage, synovial fluid, muscles, tendons, ligaments, and other tissues. These dynamic elements include relatively compliant ones (ligaments, tendons, fluid, cartilage) which allow for substantial energy absorption and storage, and relatively stiffer ones (bone) that allow for efficient energy transfer. The cartilage in a joint compresses under applied force and the resultant force displacement product represents the energy absorbed by cartilage. The fluid content of cartilage also acts to stiffen its response to load applied quickly and dampen its response to loads applied slowly. In this way, cartilage acts to absorb and store, as well as to dissipate energy.

With the foregoing applications in mind, it has been found to be necessary to develop effective structures for achieving desired load reduction, energy absorption, energy storage, and energy transfer across bones defining a joint.

In certain applications, it may be desirable to have a load manipulation device which includes parts which are not linked across a joint. Such devices may form temporarily continuous structures under certain joint motion or loading conditions and may be discontinuous in others. Such devices may provide less resistance to motion in multiple directions and thus be more compatible with natural motions of the joint being treated. By way of example, an non linked device could provide zero resistance to any joint motion when the device is in a passive, discontinuous or non loaded state while the same device could alter the joint loading our motion characteristic when it is in a continuous or active state.

Therefore, what is needed to treat joint pain is an implant device which addresses both joint movement and varying loads as well as dampening forces and energy absorption provided by an articulating joint while providing a device which includes parts extending across a joint which are not linked.

The present invention satisfies these and other needs.

SUMMARY

Briefly and in general terms, the present disclosure is directed towards treating diseased or mal-aligned body components. The present disclosure is directed towards methods and devices for treating and preserving body joints.

In one aspect of treating and preserving body joints, unloading devices are implanted under the patient's skin for relieving joint pain that do not require modification of articular cartilage. In a preferred aspect, the device is implanted under the patient's skin but outside of the joint capsule. In a particular aspect, the joint pain is caused by joint degeneration or osteoarthritis.

In one embodiment, the present disclosure addresses the pain associated with joint disease and mal-alignment. In presently contemplated embodiments, the unloading device includes a first component attached to a bone on one side of a joint and a second component attached to bone on an opposite side of a joint. The first and second components are not linked to one another but act to unload forces across a joint when members defining the joint are in extension. Biasing structure is contemplated to be provided to maintain contact between the first component and the second component. A flexible mount can also be incorporated into the unloading device so that relative longitudinal rotation of bones defining the joint can be accommodated.

In one preferred embodiment, an implanting unloading device is included in an implantable knee unloading device for a knee comprising a first member configured to be affixed to a first member of a knee joint, a second member configured to be affixed to a second member of the knee joint, mating portions of the first and second members configured to contact one another to transmit force between the first and second members, wherein the mating portions are not connected to one another and wherein the knee unloading device is configured to absorb at least a portion of the total load applied to the knee during at least 5 degrees and during no more than 60 degrees of a natural range of motion of the knee.

In another preferred embodiment, an implantable knee unloading device includes an implantable knee unloading device comprising a first member configured to be affixed to a first member of a knee joint, a second member configured to be affixed to a second member of the knee joint, mating portions of the first and second members configured to contact one another to transmit forced between the first and second members, wherein the mating portions are not connected to one another and wherein the entire knee unloading device is configured to be implanted entirely outside of the articulating surfaces of the knee. The mating portions enabling the transmission of force may also be of a defined geometry to facilitate simultaneous unloading of the knee and rotational motions about their surfaces. In addition to force transmission the mating portions may provide force absorption.

It is contemplated that a minimally invasive approach be taken to alleviate pain while preserving full motion of the bones forming a joint. The devices accomplish one or more of: absorbing energy during normal gait, reducing load on at least a portion of the natural joint, load transferring or bypassing, energy cushioning, and load sharing or redistribution. In addition, both energy dampening and shock absorption are considered in effecting such load manipulations. Further, the particular anatomy of a patient is considered in the contemplated approaches in that loads on desired portions of anatomy are manipulated without overloading healthy surfaces. It is believed that employing the approaches of the present disclosure can slow the progression of disease affecting the joint and can further improve alignment, stability, or support or enhance medial collateral ligament (MCL) or lateral collateral ligament (LCL) function.

In a preferred embodiment, the present devices adds an energy absorber to the joint to reduce energy transferred through the natural joint. The present device can be used unilaterally, bilaterally or multi-laterally around a body joint.

One particular beneficial aspect of the energy absorption systems of the present disclosure are that they are capable of absorbing a constant amount of energy from the joint independent of joint kinematics or loading conditions. In contrast, the rigid body systems of the prior art (such as a cam system) are based on the physician separating (i.e., distracting) the natural joint a given distance in the unloaded state and attaching the rigid body system. The rigid body system then maintains this distance/distraction throughout the gait cycle and through bending of the joint. To maintain this distraction, the rigid body must transfer a wide range of forces directly depending on joint kinematics.

Another particularly beneficial aspect of the present energy absorption systems is that the absorption system may be designed to absorb, dissipate and/or transfer energy at different rates or positions in the gait cycle thereby enabling customization of the system to the specific need. Considering the knee joint by way of example, the system may be designed to absorb severe sudden impact loads (such as jumping) and dissipate these loads after the impact event. This mode of operation is akin to the natural role of cartilage. Conversely, the system can be designed to behave primarily as an energy transfer unit during high rates of knee motion (e.g. sprinting/running) but act as an energy absorber during normal rates of motion (e.g. walking).

Yet another particularly beneficial aspect of the energy absorption system of the present disclosure is that the absorption system may also be tuned to occur at particular points in the gait or flexion cycle depending on the disease state. For example, an individual with concentrated loading at heel strike may only require absorption at this phase of knee motion so the system may be adjusted to act only during this region of the gait cycle. Alternatively, an individual may have focal loss of cartilage on the posterior aspect of the femoral condyle and so stair climbing or kneeling becomes painful or problematic. In this scenario, the system would be adjusted to absorb energy in the kinematic positions necessary and thereby maintaining the normal knee energy transfer outside of supporting the diseased locations.

In another beneficial aspect, components of the system are designed for easy removal and, if necessary, replacement while others are intended for permanent fixation. The permanent components are fixation base components which can have bony ingrowth promoting surfaces and are responsible for fixation of the system to the skeletal structure. The removable components include the mobile elements of the system such as the energy manipulation members and/or the pivots or ball joints.

Various joints of the body can be treated employing the systems and methods of the present invention. In particular, articulating bones involved in synovial joints can benefit from the present invention. Accordingly, there are contemplated applications to the joints in the knee, ankle, shoulder, hip, hand and wrist. Further, the present invention can have applications in treating cartilaginous joints such as those found in the spine.

In a further aspect, the present disclosure seek to accomplish 1 to 40% energy or load reduction while maintaining full motion of the body parts. A 5 to 20% energy or load reduction has been postulated to be desirable in certain circumstances to accomplish the alleviation of pain without approaching undesirable load shielding. The devices further provide greater energy manipulation during junctures of highest loads placed between body parts as well as less energy manipulation when loads between members decrease. In this way, the devices complement the action of body parts such as those found at joints.

In some joints, it is desirable that 100% of the energy be absorbed by the device(s) In such cases, it may be desirable to have the devices placed bilaterally on either side of the joint. In the lower extremity, in severe cases, 100% energy absorption is achievable, however this may expose the device to more wear and shorter life. It is contemplated therefore that the devices may be considered temporary, being implanted for a defined service life and then removed or replaced. Some patients may accept this if the device is able to bridge the patient through a difficult period and it is easily replaced or removed without impacting the patients ability to receive a total joint replacement later.

In another embodiment, an energy absorption device is implanted at a diseased joint to restore cyclic, physiological-like loading thereby protecting chondrocytes from load induced apoptosis. In yet another embodiment, an energy absorption device is implanted at a diseased joint to facilitate at least a partial recovery of morphological and ultra-structural aspects in osteoarthritic articular chondrocytes. An energy absorption device can also be implanted adjunctively with a cartilage repair procedure such as mosaicplasty, osteochondral allograft transfer, autologous chondrocyte implantation or microfracture. Such an adjunctive procedure would enable less strict rehabilitation regimes while simultaneously protecting the graft and stimulating it with appropriate motion. Moreover, an energy absorption device can be implanted in conjunction with a uni-compartmental joint replacement prosthesis or total joint replacement prosthesis. Such combination procedure will reduce wear rates by reducing the loads and contact forces between surfaces of the joint prosthesis.

Rotation point location of the energy manipulation member on the femur is determined in part by the mechanism of the device. The inventors of the present invention have discovered regions on the femoral chondyle in which a rotation point on the device relative to a tibial rotation point along a line normal to the ground from the femoral rotation point will either have minimal displacement, lengthening of the device or shortening of the device as the joint moves from full extension to flexion. Therefore, if the desired device is to function by elongation its rotation point will be located in the appropriate region. Conversely, if the desired device is to function by compression its rotation point will be located in a different appropriate region.

In one specific embodiment, the present invention is embodied in a device utilizing an element, or elements functioning as a unit, which responds to bending or changes in elongation. In an application to a knee joint, this device spans the tibiofemoral joint and be anchored into the tibia and femur. Further, the device is used to take on some of the loading experienced by the articular surfaces of the tibiofemoral joint, thus unloading the joint. In one embodiment, the device is designed to off load the joint during knee extension. Unloading in this phase is governed by the compression of the device—increased compression yields increased joint un-loading. The device is anchored in a position which ensures device elongation resulting from knee flexion. As the knee moves into flexion, the device is un-compressed and will cause little to no joint unloading. The device may have other features which ensure correct device alignment, and prevent against buckling, as the device transitions into a compressed state. The device can also be configured to provide unloading during flexion.

The energy absorption system can be comprised of permanent fixation base components and removable energy absorption. The permanent fixation base components incorporate a bone ingrowth promoter on their bone contacting surface (e.g. porous surface, calcium phosphate coating, textured surface etc.). It is important to stimulate this interface using moderate loads to ensure the creation of a bony interface, however overloading the interface prematurely may prevent bone ingrowth. To facilitate bony ingrowth, it is possible that the system will be implanted in a mode of operation whereby it is absorbing small amounts of load to create a moderate load condition at the interface. A subsequent simple procedure will be completed at an appropriate time post implantation to adjust the energy absorption settings to absorb higher amounts of load.

Other features and advantages of the present disclosure will become apparent from the following detailed description, taken in conjunction with the accompanying drawings, which illustrate, by way of example, the principles of the invention.

BRIEF DESCRIPTION OF THE DRAWINGS

FIG. 3 is a side view, depicting the device of FIG. 1 on bones of a joint which are in flexion;

FIG. 4 is an enlarged view, depicting components of the device of FIG. 1;

FIG. 5 is an enlarged cross-sectional view, depicting further details of the device of FIG. 1;

FIGS. 16B and 16C are side views of the device of FIG. 16A with the knee joint in extension and flexion;

FIG. 26 is a side view of a further unlinked unloading device with convex mating portions and resilient absorbers;

FIG. 27 is a side view of a cam and follower version of an unlinked unloading device;

FIG. 28 is a side view of a spring beam version of an unlinked unloading device;

DETAILED DESCRIPTION OF THE PREFERRED EMBODIMENTS

Figure 1:
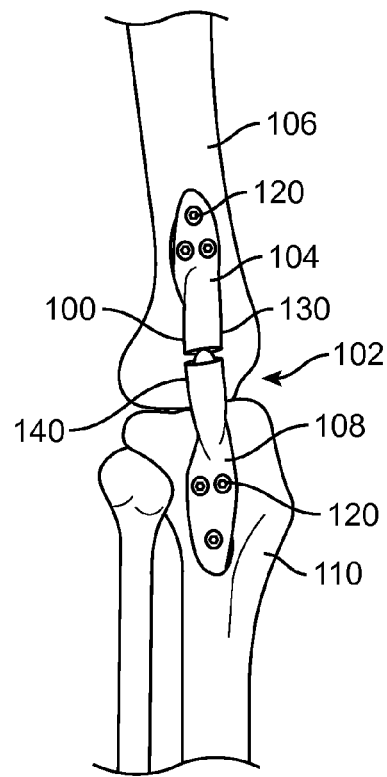
FIG. 1 is a side view, depicting one preferred approach to an unlinked unloading device.
Figure 2:
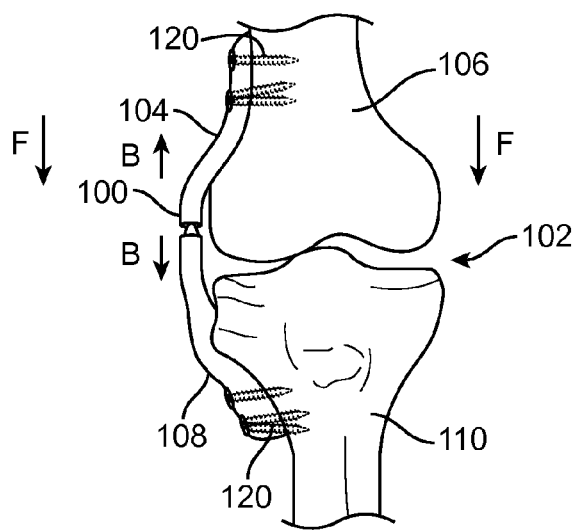
FIG. 2 is a front view, depicting the device of FIG. 1.

Referring now to the drawings, which are provided by way of example and not limitation, the present invention is directed towards apparatus and methods for treating body tissues. In applications relating to the treatment of body joints, the present invention seeks to alleviate pain associated with the function of diseased or malaligned members forming a body joint. Whereas the present invention is particularly suited to address issues associated with osteoarthritis, the energy manipulation accomplished by the present invention lends itself well to broader applications. Moreover, the present invention is particularly suited to treating synovial joints such as the knee and shoulder. However, it is also contemplated that the apparatus and method of the present invention can be employed to treat various other joints of the body such as those of the spine, ankle, hip, hand and feet.

In one particular aspect, the present invention seeks to permit and complement the unique articulating motion of the members defining a body joint of a patient while simultaneously manipulating energy being experienced by both cartilage and osseous tissue (cancellous and cortical bone). Approaches involving varying energy absorption and transfer during the loading and pivoting of the joint and selecting a geometry for the energy absorption assembly to provide necessary flexibility are implemented into various embodiments of the present invention. Certain of the embodiments include geometry which accomplishes variable energy absorption designed to minimize and complement the dampening effect and energy absorption provided by the anatomy of the body, such as that found at a body joint. It has been postulated that to minimize pain, unloading or absorption of 1-40% of forces, in varying degrees, may be necessary. Variable unloading or absorption in the range of 5-20% can be a target for certain applications. In certain specific applications, distraction is employed in the energy manipulation approach.

In one particular approach, a spring assembly is contemplated to manipulate or absorb forces between body parts and in particular between the bones of a joint. Assemblies described herein utilize one or more elements which respond to bending or changes in elongation to off-load the articular surfaces of a joint and treat joint afflictions such as osteoarthritis. Certain of the assemblies can incorporate features which insure correct device alignment and prevent against buckling as the member transitions between compressed and uncompressed states.

Turning now to FIGS. 1-5, there is shown one preferred embodiment of an unlinked implantable joint unloading device 100. This as well as the other described approaches are intended to be implanted subcutaneously and entirely outside the articulating surface of a joint. As shown, the unloading device 100 is positioned across a knee joint 102. However, as stated, it is to be appreciated that the unloading devices described herein can be employed to treat other areas of a patient's body.

Conventional surgical or minimally invasive approaches can be taken to gain access to the body joint or other anatomy requiring attention. Arthroscopic approaches are contemplated when reasonable to both implant the energy manipulation assembly as well as to accomplish adjusting an implanted assembly if needed.

The unloading device 100, as shown in FIG. 1, includes a first member 104 attached to a first bone 106 of the joint 102 and a second member 108 attached to a second bone 110 of the joint 102. Mating portions of the members 104, 108 are designed to transmit forces therebetween. In one specific approach, the mating portions of the first and second members are confined to primarily pivoting motion, without substantial translational motion. Various fasteners 120 in the form of compression and/or locking screws are employed to attach the first and second members 104, 108 to bone on opposite sides of the joint. The fasteners 120 can be angled at varying trajectories to securely attach the members 104, 108 to anatomy.

Biologically inert materials of various kinds can be employed in constructing the unloading devices of the present invention. For example, the first and second members can be titanium or titanium alloy, cobalt chromium alloy, ceramic, high strength plastic such as polyetheretherketone (PEEK) or other durable materials. Combinations of materials can also be used to maximize the properties of materials for different part so the unloading device. At the bone interface surfaces, the materials can be coated with a material which promotes osseointegration. At the wear surfaces, the material may include a combination of metal-on-poly, metal-on-metal, metal-on-ceramic or other combinations to minimize wear.

The first and second members 104, 108 each include terminal ends 130, 140 which define mating portions. As shown in FIG. 4, the terminal end 130 of the first member 104 includes a generally conical recess 132 sized and shaped to receive a conical projection 142 extending from terminal end 140 of the second member 108. The conical recess and projection structure aids in seating the mating surfaces of the first and second members 104, 108 by guiding the surfaces into a proper seated position.

It is to be appreciated that other terminal end configurations are also possible. For example, a ball and socket or dome arrangement can be incorporated into the terminal ends and also provides a self centering type of mating arrangement. Other mating configurations, such as a cylinder and plate type mating surface or a pin and trough type mating configuration can also be used. The mating structures of the first and second members 104, 108 are not connected, in that, the terminal end 130 of the first member 102 is not fixed to the terminal end 140 of the second member 108. The unlinked, non-connected device 100 provides unloading to the joint during a portion of the motion of the joint when the terminal ends are in contact and provides no unloading during a portion of the joint motion where the terminal ends are not in contact. The portion of joint motion at which the terminal ends are in the mating configuration is determined based on the particular joint anatomy and disease. In the example of a knee joint, unloading is provided during the extension stage of the gait cycle and the mating portions are separated and not providing any unloading of the joint at some desired angle of flexion.

In one contemplated embodiment, the unloading device 100 can absorb at least a portion of a load found within a knee joint during at least five degrees and no more than sixty degrees of natural motion of the knee. For example, the device 100 can provide unloading from extension through at least five degrees and up to sixty degrees of flexion. Further, the first and second members 104, 108 can be configured to remain in contact throughout a full range flexion of a joint or can be arranged to be disengaged during portions of flexion.

Referring specifically to FIG. 5, there is shown a piston and sleeve arrangement that can be incorporated into the unloading device acting as an energy absorber. That is, the second member 108 of the unloading device 100 can include a piston and sleeve structure acting as an energy absorber as well as a biasing member for the conical or other terminal end 142 of the second member 108. In the embodiment of FIGS. 1-5 the conical terminal end 142 of the second member 108 is located on the end of a piston 152 of the energy absorber. The piston 152 is biased toward the first member 108 by the one or more springs described below. It is to be understood that the first member 104 can alternatively include the piston and sleeve absorber arrangement, or both the first and second members 104, 108 can include absorber arrangements.

Additional examples of absorber structures and structures for fixing the absorber structures to bone are describe in U.S. Patent Application Publication Nos. 2008/027556; 2008/0275562 and 2009/0318976 which are incorporated herein by reference in their entirety.

In the particular embodiment illustrated, the second member 108 can include an outer sleeve structure 150 for receiving the cylindrical piston member 152 which terminates with the conical projection 142. Energy absorption is accomplished primarily by way of an energy absorber spring 154 which absorbs forces during a portion of the natural motion of the joint being treated. A biasing spring 156 is also configured within the sleeve 150. The biasing spring 156 facilitates controlling the positioning of the cylindrical member 152 so that it is placed in apposition with the terminal end 132 of the first member 104. In one approach, it is contemplated that while unconnected, the first and second members 104, 108 remain in contact through a substantial portion of the natural motion of the joint (See FIG. 3) while providing biasing force over a smaller range of motion of the joint.

The biasing spring 156 can have a lower spring constant or stiffness than the energy absorption spring 154. The biasing spring 156 can also have a greater length than the energy absorption spring 154 and can participate in the energy absorption or loading function of the device. One or more of the biasing and energy absorption springs can also be omitted in a specific device if desired. The piston 152 can be provided with a stop which prevents the piston from extending out the sleeve 150 more than a predetermined amount.

Figure 6:
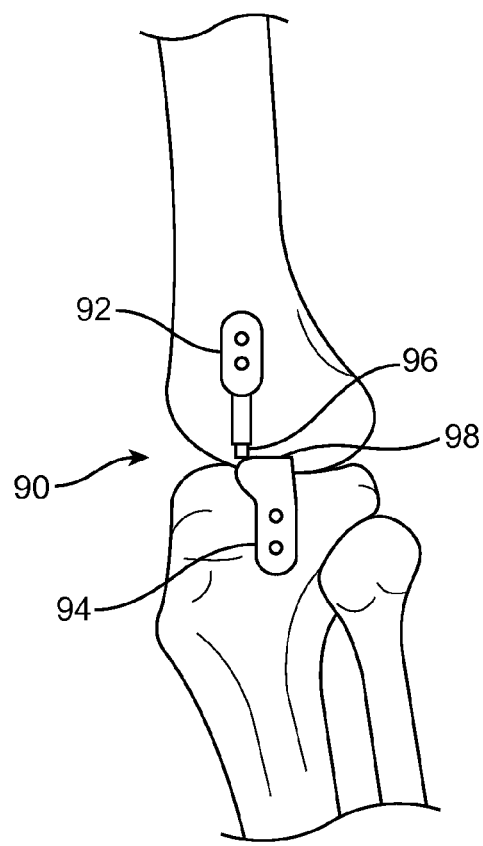
FIG. 6 is a side view, depicting an embodiment of a device incorporating pivoting and disengaging structure.
Figure 7:
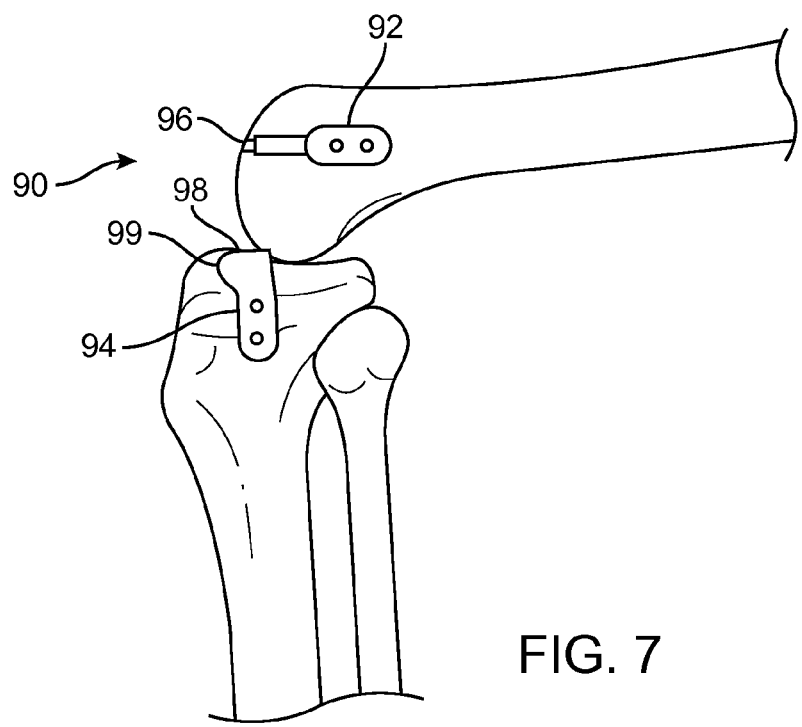
FIG. 7 is a side view, depicting the embodiment of FIG. 6 with the anatomy in an articulated position.

FIGS. 6 and 7 depict an embodiment of an energy manipulation assembly 90 including a first part 92 and a second part 94, the first and second parts only engaging when the body anatomy approaches an aligned configuration. In the case of a knee joint, this aligned configuration is at the extension phase of the gait cycle. In this way, energy manipulation or unloading is achieved in extension but not in flexion. The assembly 90 includes a pin 96 which can be biased by one or more absorber and/or biasing springs. The pin 96 is configured to mate against a contacting surface 98 of the second part which may be a flat surface, as shown. Alternatively, the contacting surface 98 may be a trough shaped or a concave curved surface. An anterior end 99 of the contacting surface 98 is preferable curved to guide the pin 96 onto the contacting surface. As an alternative to the spring biased pin 96, the contacting surface 98 can be provided with absorber and/or biasing springs or both the pin and contacting surface can function as absorbers.

Figure 8:
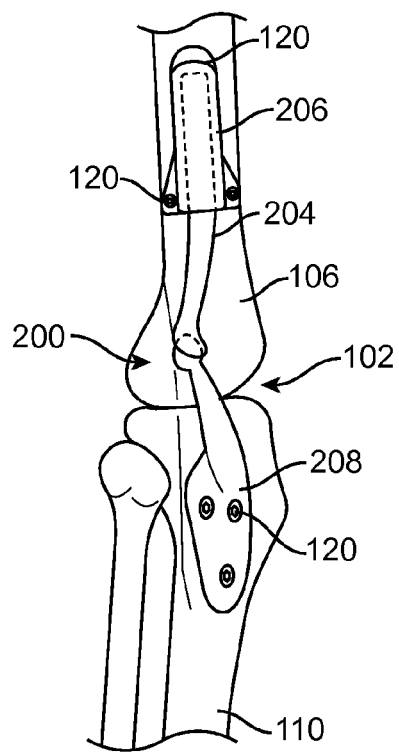
FIG. 8 is a side view, depicting another preferred approach to an unlinked unloading device.
Figure 9:
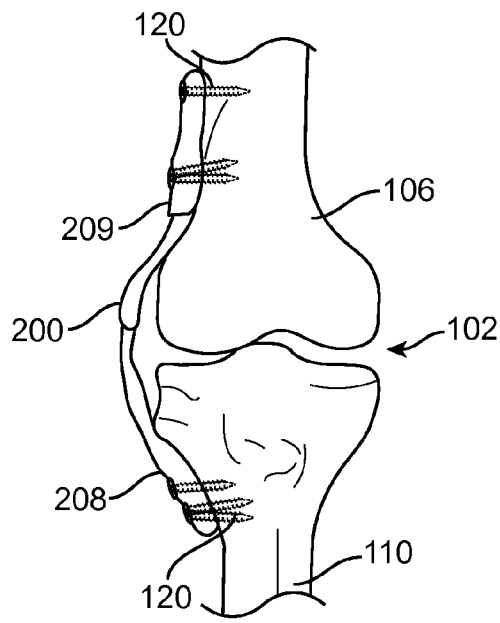
FIG. 9 is a front view, depicting the device of FIG. 8.
Figure 10:
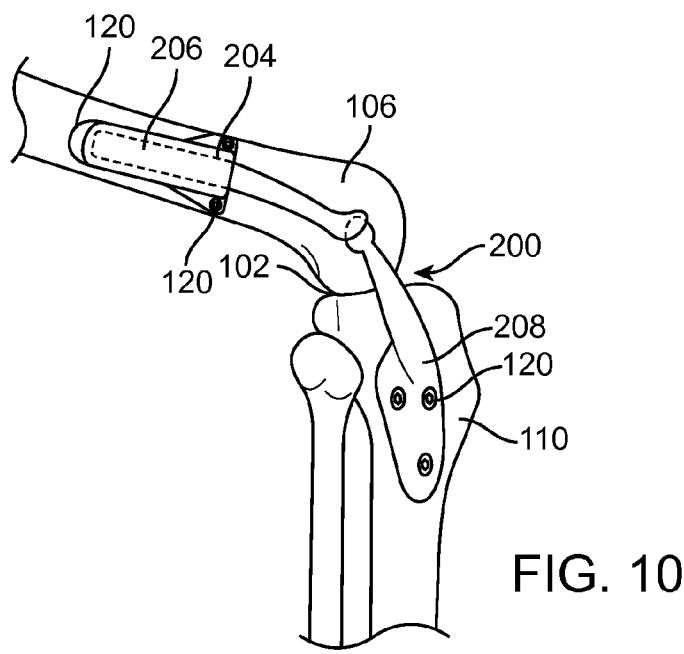
FIG. 10 is a side view, depicting the device of FIG. 8 on bone joints in flexion.
Figure 11:
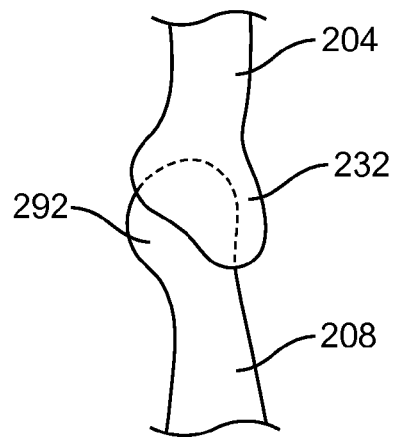
FIG. 11 is an enlarged view, depicting the engagement of first and second components of the device of FIG. 8.

Turning now to FIGS. 8-11, there is shown another preferred approach to an unlinked implantable unloading device 200. Similar to the previously described devices, the unloading device 200 can be affixed to bone using fasteners 120 angled at varying trajectories in order to accomplish a secure attachment. This embodiment includes a first member or component 204 attached to the first bone 106 of a joint 102 and a second member 208 attached to the second bone 110 of the joint 102. As best seen in FIG. 11, the first member 204 has a terminal end defining a socket like structure 232 and the second member 208 includes a ball-like terminal end 242. One or more of the first and second members 204, 208 can include the piston and sleeve absorber arrangement disclosed in FIG. 5 or another absorber configuration. As shown in FIGS. 8-10, an absorber 206 is provided in the first member 204 and biases the socket like structure 232 toward the second member 208. In addition to unloading a portion of the load normally borne by the joint, the absorber 206 can provide a biasing member configured to allow the members to remain in contact during significant portions of the natural motion of the joint being treated (See FIG. 10).

Figure 12:
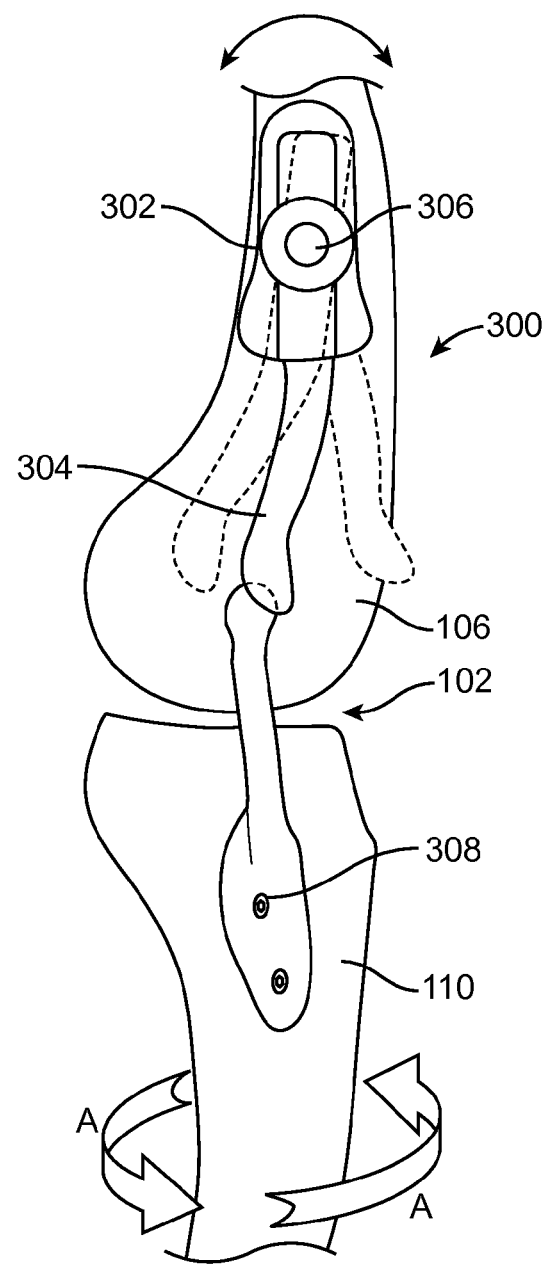
FIG. 12 is a side view, depicting a flexible mount device.

As shown in FIG. 12, the various contemplated unloading devices can further include a flexible mount 302 for a first member 304 of an alternative approach to an unloading device 300. In this way, natural longitudinal or axial rotation of a second member 110 of a joint 102 with respect to a first member 106 of the joint 102, can be accommodated by the flexible mount 302. The flexible mount 302 can assume various configurations. For example, the first member 304 can be arranged to rotate about a pivot 306 fixed to bone. The assembly can further incorporate elastomeric or other flexible material permitting rotation or pivoting of the first member 304. The rotation of the first member 304 about the pivot 206 can be limited as needed to accommodate varus/valgus rotation of the joint (not shown) and rotation of one of the members of the joint as shown by the arrows A in FIG. 12.

Thus, in one contemplated approach, the first member 304 of the implantable unloading device 300 can be properly positioned to contact the second member 308 of the device 300 attached to the second bone 110 of the joint even when there has been no flexion of the members defining the joint 300. By remaining in contact, from full extension through some desired angle of flexion, the members defining the unloading device 300 can perform the desired load manipulation. It is to be further understood that such a flexible mount can alternatively be incorporated into the second member 308 or into both first and second members attached across a joint.

Figure 13:
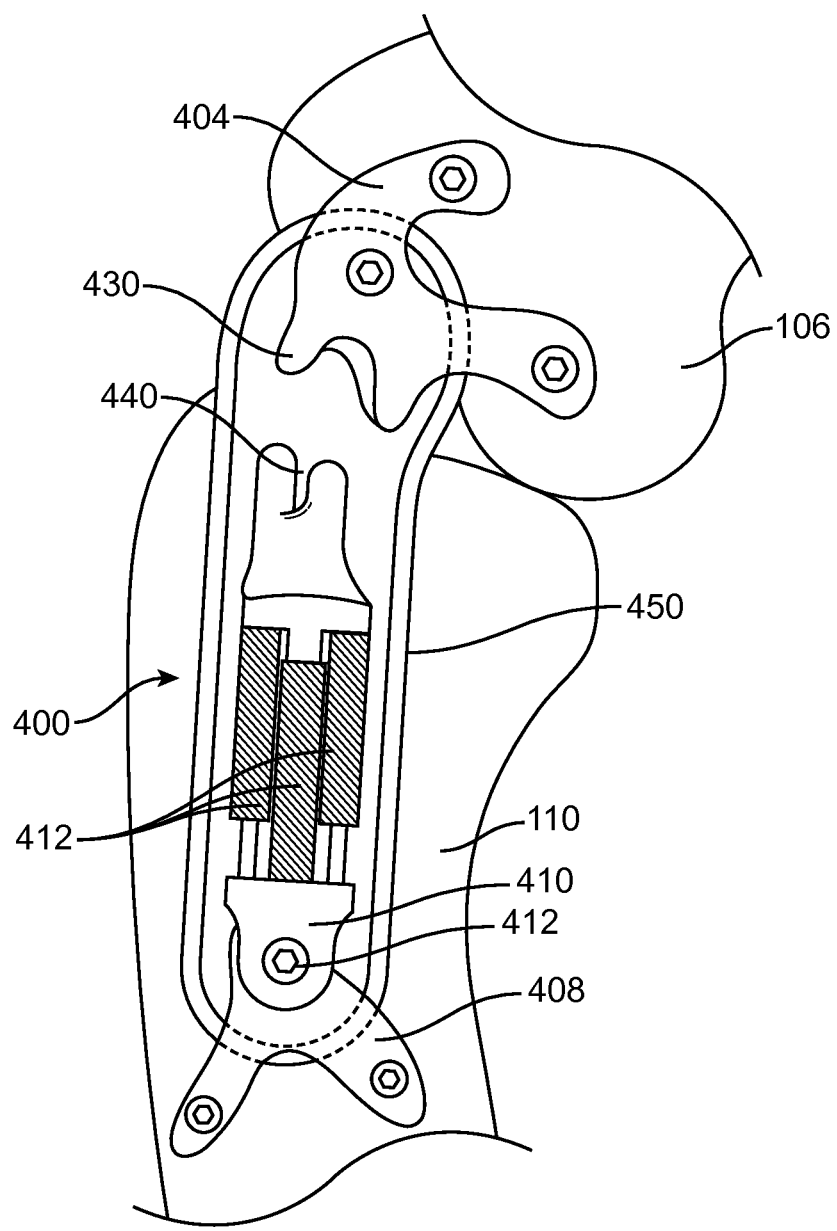
FIG. 13 is a side view of an additional embodiment of the unlinked unloading device.

FIG. 13 shows another embodiment of an implantable unloading device 400 mounted on a femur 106 and tibia 110. The unloading device has a first member 404 fixed to the femur and a second member 408 affixed to the tibia. An absorber 410 is connected by a pivotal connection 412 to the second member 308. Alternatively, the absorber 410 can be connected to the first member 404. Terminal ends 430 and 440 of the unloading device 400 are separable saddle-shaped portions that are configured to engage one another and can act like a hinge. The saddle-shaped portions 430, 440 can also be described as a hinge joint. The device 400 can include a flexible sheath 450 surrounding the absorber 410 and the mating portions 430, 440.

Figure 14:
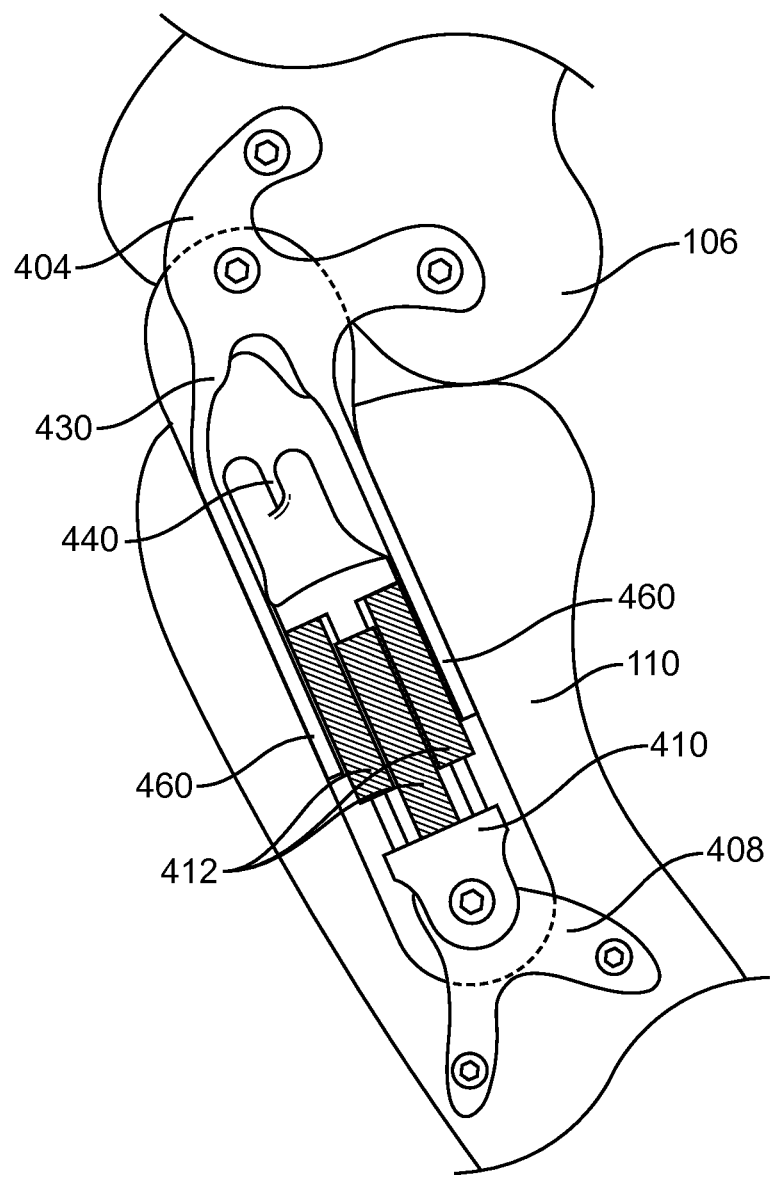
FIG. 14 is a side view of an unlinked unloading device with alignment tracks.

The embodiment of FIG. 13 or any of the other embodiments can include two or more tracks or landing strips 460 which maintain alignment as the mating portions 430, 440 approach each other (FIG. 14). The tracks 460 can be formed of a flexible material and can be attached to the first or second member. The separate tracks 460 can be replaced with a tubular member which can prevent tissue impingement and function in a manner similar to the sheath 450. The embodiment of FIGS. 13 and 14 includes an absorber having three parallel springs 412. However, other numbers and arrangements of springs in an absorber are also contemplated.

FIGS. 15A-D illustrate another embodiment of an unlinked implantable knee unloading device 500 including a combination of an open sided spring 510 and a piston 520 which can move into and out of the open sided spring. The unloading device includes a first member 504 attached to a first bone 106 of the joint and a second member 508 attached to a second bone 110 of the joint 102 in a suitable manner, such as by a plurality of bone screws. The piston 520 may be joined to the first member 504 by a pivot 506, such as a universal joint. The open sided spring 510 may be a machined spring, as shown, or may be another type of spring. An interior of the spring 510 and an exterior of the piston 520 for mating portions designed to transmit forces between the first and second members 504, 508. Although the spring 510 is shown fixed to the second member 508, alternatively, the spring may be connected by an additional pivotal connection. The ability of the piston 520 to move into and out of the spring 510 during motion of the joint, can reduce wear during flexion.

Figure 15A:
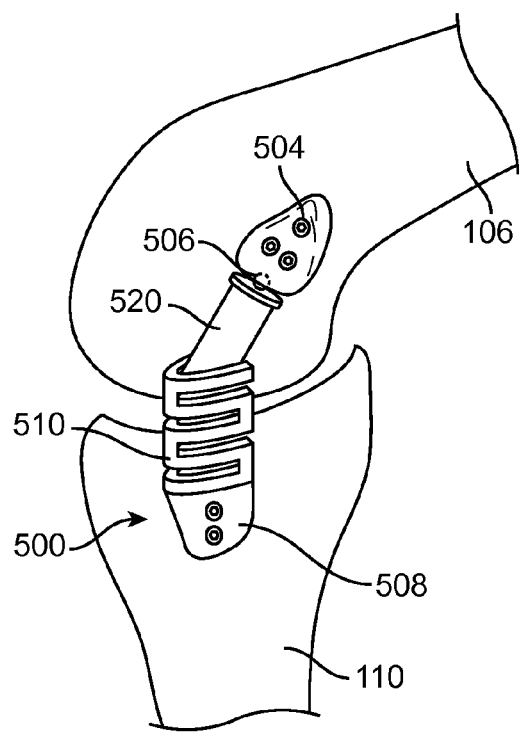
FIG. 15A is a side view of another embodiment of the unlinked unloading device shown on a knee joint in flexion.
Figure 15B:
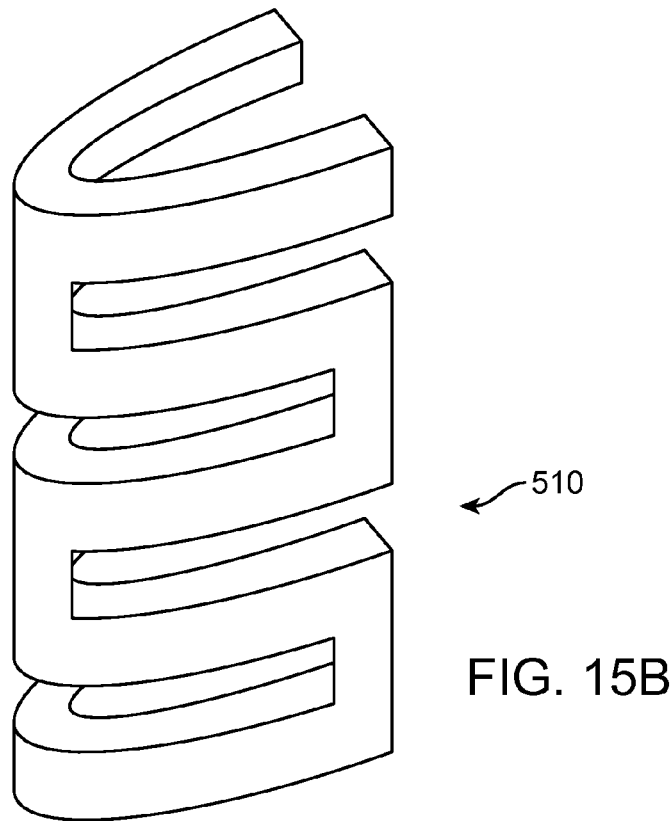
FIG. 15B is a perspective view of the spring element of the device of FIG. 15A.
Figure 15C:
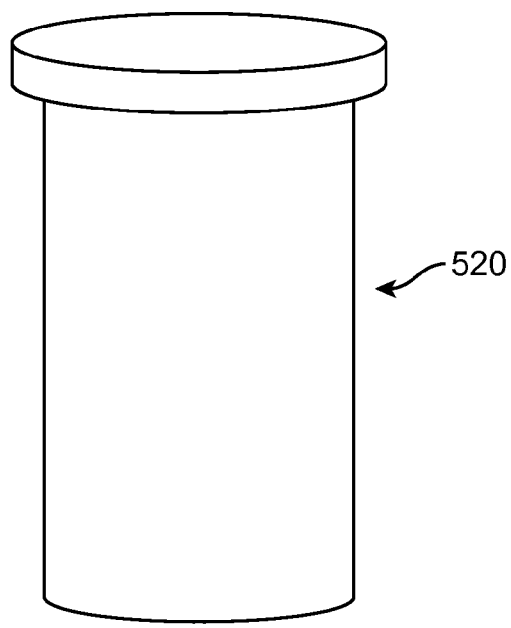
FIGS. 15C and 15D are side and front views, respectively, of the piston for use with the spring element of FIG. 15B.
Figure 15D:
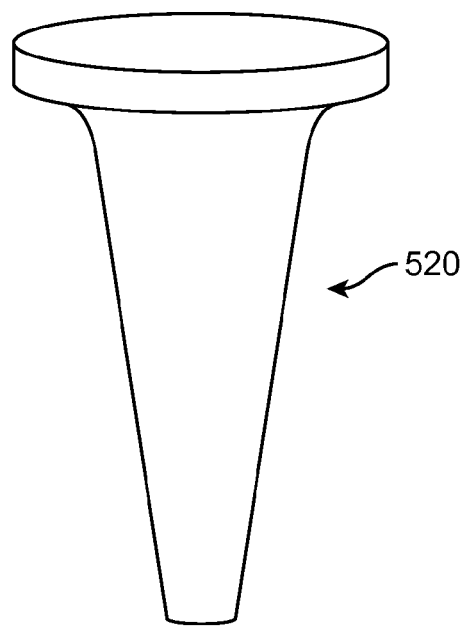

The piston 520 shown in FIGS. 15C and 15D has a tapering profile when viewed from the front of the joint. The tapering profile provides a varying flexibility to the piston along the piston length with a most flexible distal portion and more rigid proximal portion. The more flexible distal portion of the piston 520 allows the piston to slide more easily into and out of the spring 510 due to this flexibility. The tapering profile can also help to guide the piston 520 smoothly into the spring 520.

Figure 16A:
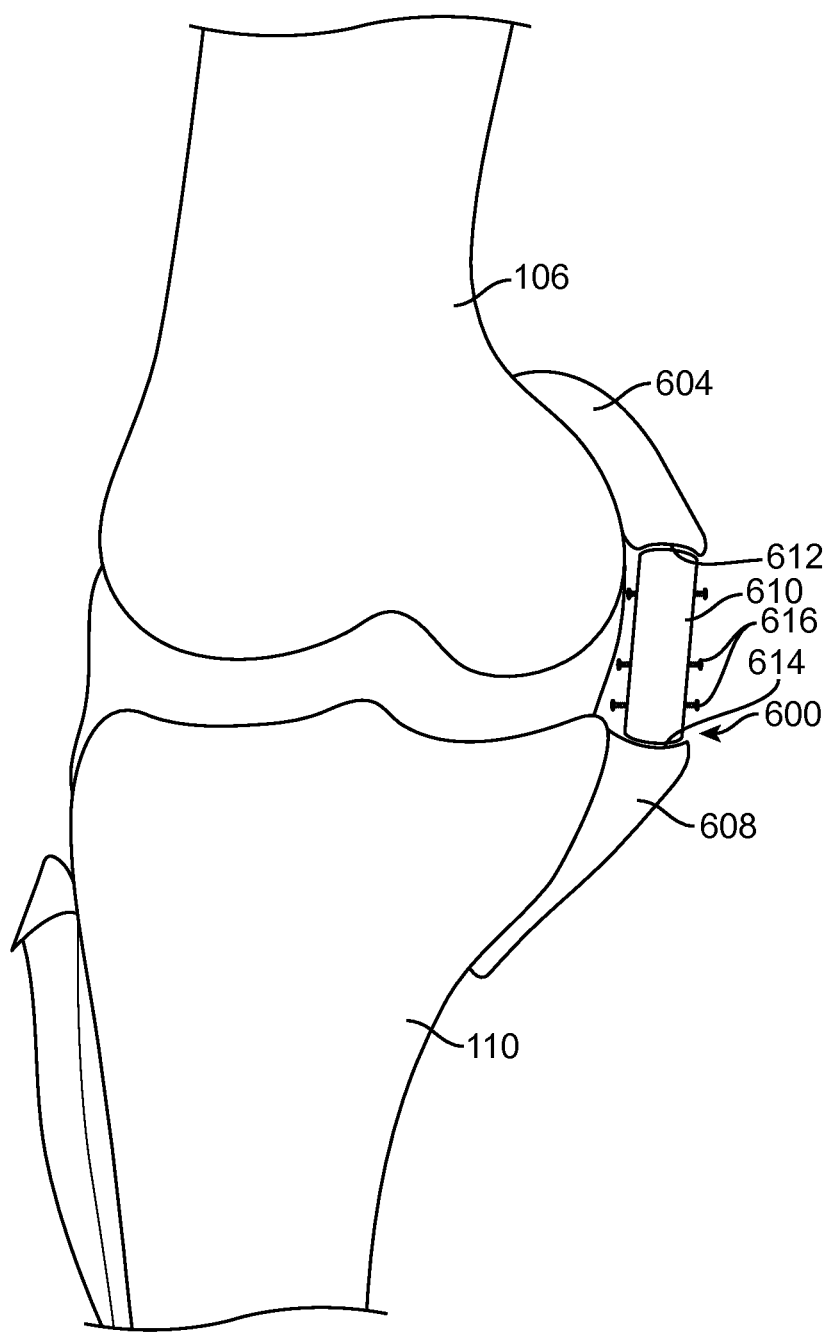
FIG. 16A is a front view of a further embodiment of an unlinked unloading device with a tethered absorber element.

FIGS. 16A, 16B and 16C illustrate another embodiment of an unlinked unloading device 600 having a tethered floating absorber element 610. The tethered unloading device 600 includes first and second members 604, 608 fixed to the first and second bones 106, 110. The first and second members 604, 608 have bearing surfaces 612, 614 configured to engage the absorber element 610. The absorber element 610 is a compliant member which is positioned between the bearing surfaces 612, 614 and configured to absorb a portion of the load normally applied to the natural joint. The absorber element 610 may be formed of a complaint material or may be formed from one or more spring and piston assemblies as described with respect to other embodiments herein.

The absorber element 610 can be tethered in place to surrounding tissues by a plurality of tethers 616. These tethers may include eyelets, barbs, mesh, screws or other features which allow the attachment the absorber element 610 to the surrounding tissue by sutures, staples or the like. Alternately, the tethers may connect the absorber element 610 to the bases, or to one or more elements secured to the bone. The tethers 616 may also be formed by creating a textured surface on a part or all of the absorber element 610 which allows soft tissue ingrowth and attachment to the textured surface. The textured surface may be in the form of a porous coating, a mesh, a barbed surface or other textured surface features formed in or on the surface of the absorber element 610.

Figure 17A:
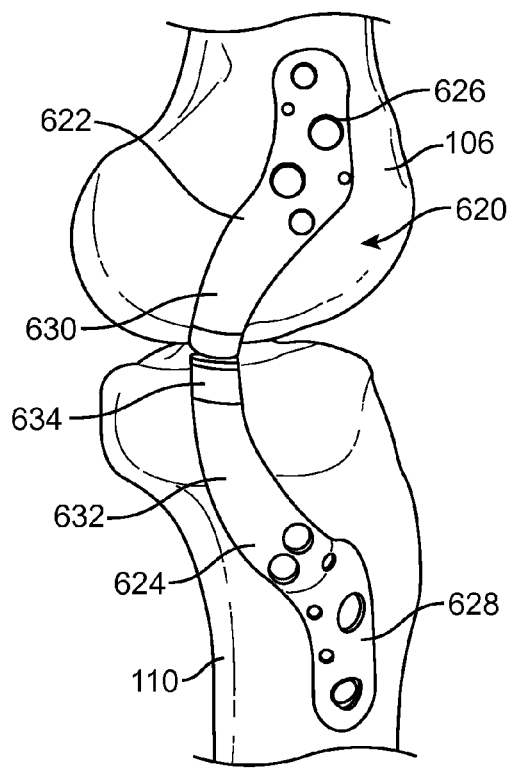
FIG. 17A is a side view of another embodiment of an unlinked unloading device with a resilient material for compliance.
Figure 17B:
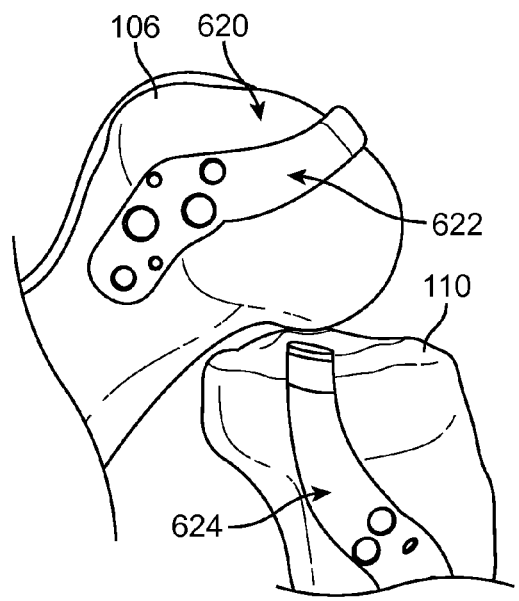
FIG. 17B is a side view of the device of FIG. 17A with the knee joint shown in flexion.

FIGS. 17A and 17B show an implantable knee unloading device 620 including a first member 622 configured to be affixed to the femur 106 and a second member 624 configured to be affixed to the tibia 110. The first and second members 622, 624 each include a base 626, 628 for securing to the bone and an extension 630, 632 which is formed integrally with the base and extends from the base toward the other member and is positioned over the knee ligaments present. As shown in FIGS. 17A and 17B, the extensions 630, 632 contact one another at mating surfaces to provide unloading of the joint when the knee joint is in extension and provides no joint unloading beyond about 20 degrees of flexion. The mating surfaces in one variation include a polymer mating surface of the first member 622, such as UHMWP or PEEK and a metal mating surface of the second member 624, such as cobalt chrome. One or more of the members can include a compliant member, such as a resilient silicon segment 634 of the second member 624. Alternatively, the compliant member may be another type of resilient material or a spring member.

Figure 18B:
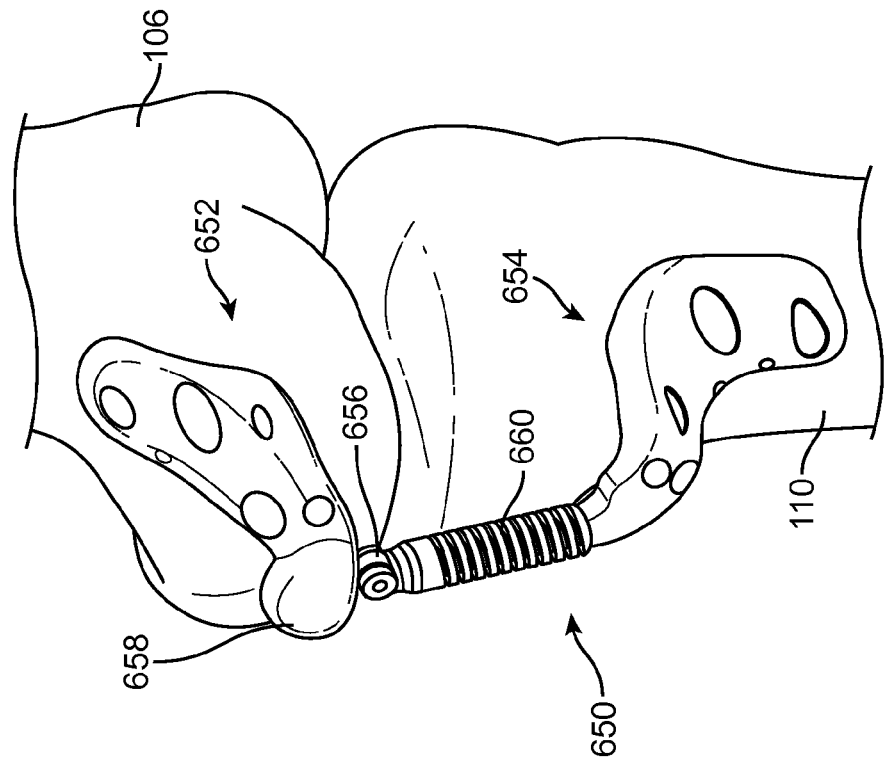
FIG. 18B is a perspective view of the device of FIG. 18A showing the follower roller.
Figure 18A:
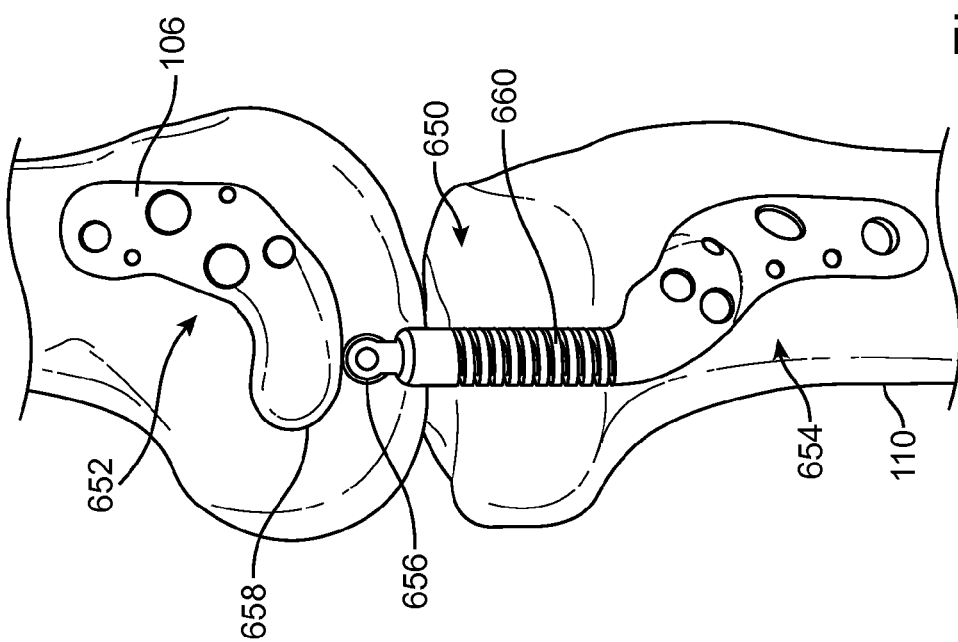
FIG. 18A is a side view of a further embodiment of an unlinked unloading device having a spring loaded follower.

FIGS. 18A-8C illustrate another embodiment of an implantable knee unloading device 650 having a first member 652 forming a cam surface and a second member 654 forming a follower. As can be seen in FIG. 18B, the follower is shown in the form of a roller 656 which travels along a contoured cam surface 658. The follower 656 is provided with an absorber 660 shown here in the form of a spring loaded piston and arbor assembly.

Figure 18C:
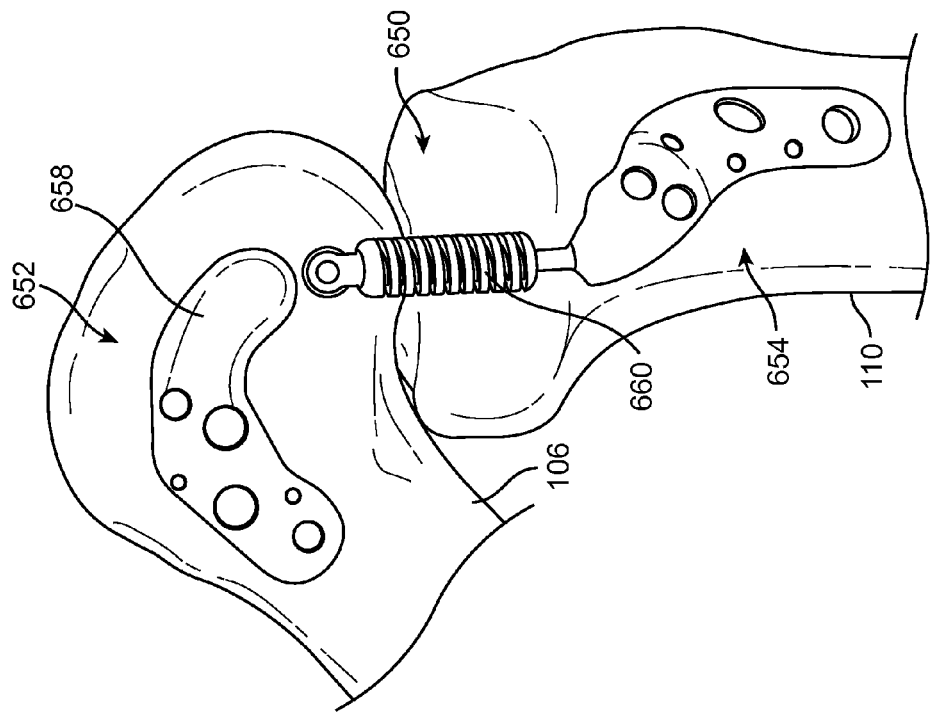
FIG. 18C is a side view of the device of FIG. 18A with the knee joint shown in flexion.
Figure 18D:
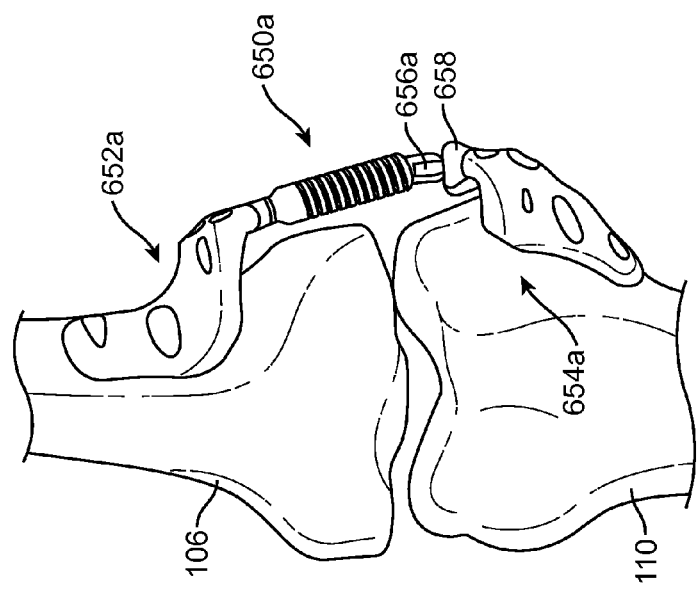
FIG. 18D is a front view of a device similar to that of FIG. 18A with the cam and follower positions reversed.

FIG. 18D illustrates an alternative version of the cam unloading device of FIGS. 18A-18C in which the cam surface 658a is provided on the second member 654a and the follower with roller 656a is provided on the first member 652a.

Figure 19:
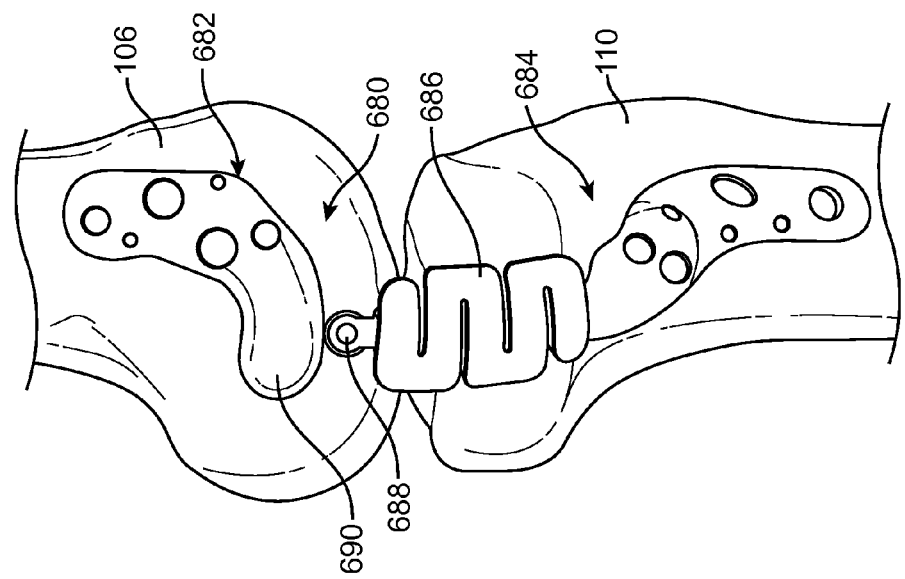
FIG. 19 is a side view of an alternative embodiment of an unlinked unloading device with contoured spring follower.

FIG. 19 illustrates another version of a cam unloading device 680 having a first member 682 forming a cam surface 690 and a second member 684 forming a follower 688. The follower 688 is shown in the form of a roller which travels along the contoured cam surface 690. The follower 688 is provided with compliance via a contoured absorber spring 686 which may be in the form of a polymer (i.e. PEEK or UHMWP) spring.

Figure 20:
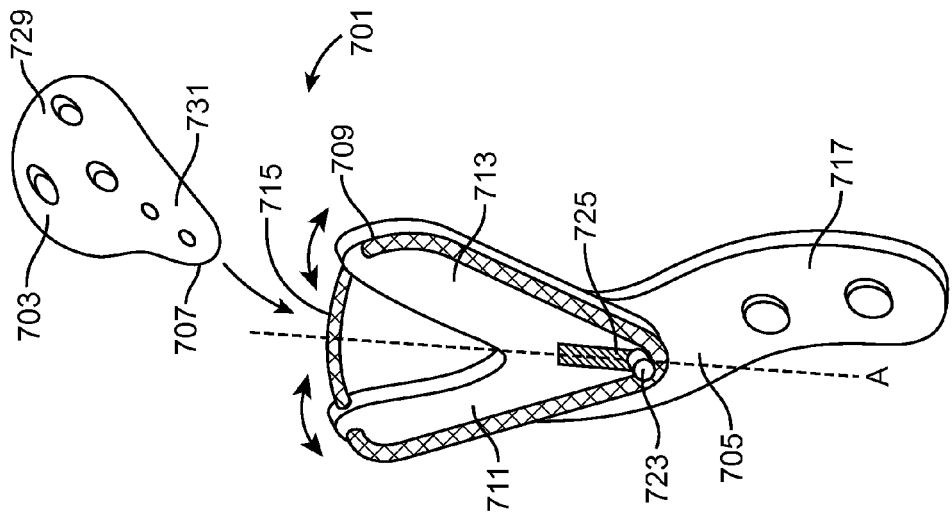
FIG. 20 is a perspective view of another embodiment of an unlinked unloading device with a flexible tension member.

FIG. 20 shows an implantable knee unloading device 701 for a knee according to another aspect of the present invention. The device 701 comprises a first member 703 configured to be affixed to a first member of a knee joint; and a second member 705 configured to be affixed to a second member 110 of the knee joint. The second member 705 comprises a mating portion 707 comprising a flexible tension member 709 extending between two arms 711 and 713. Mating portions 715 and 707 of the first and second members 703 and 705 are configured to contact one another to transmit forces between the first and second members, and the mating portions are not connected to one another.

On the second member 705, the two arms 711 and 713 extend from a base 717 configured to be affixed to the second member 110 of the knee joint. Ordinarily, at least one of the two arms 711 and 713 is adapted to deflect relative to a longitudinal axis A of the base 717 when the mating portions 715 and 707 of the first and second members 703 and 705 contact one another to transmit ordinary forces between the first and second members. More typically, both of the arms 711 and 713 will be adapted to deflect relative to the base 717. The expression "ordinary forces" is defined for purpose of the present application as the ordinary forces to which a knee joint is likely to be subject during normal use by a given individual over at least a part of the normal range of motion of a knee. As persons skilled in the art will appreciate, for a particular person, ordinary forces may differ depending upon factors such as the person's weight. As seen in FIG. 20 the flexible tension member 709 can comprise a cable, such as a Nitinol cable 719 extending between the two arms 711 and 713, although other forms of tension members can be provided, such as a flexible membrane or band or other resilient member. When a cable 719 in the form of an endless cable is provided, the arms 711 and 713 can be provided with tracks 721 in which the cable can be slidable. Alternatively, rotatable wheels or rollers (not shown) can be provided over which the cable 719 can be moved. The cable 719 may, alternatively, be fixed at one or more points.

The cable 719 shown in FIG. 20 extends around and contacts a tensioning pin 723. The tensioning pin 723 can be attached to a resilient member arranged to be compressed when a load is applied to the tension member. For example, the resilient member can be in the form of a spring loaded piston 725. When a load is applied to the tension member 709, one or both of the arms 711 and 713 may deflect and/or the spring associated with the piston of the tensioning pin 723 can be compressed to absorb the load. The tensioning pin 723 can be biased away from the first member by a biasing structure which can take on different forms. Instead of a spring loaded piston 725, the biasing structure can be in the form of, for example, a resilient member, such as a compressible rubber element, a leaf spring, a coil spring, or the like. The biasing structure can be located inside or outside of the second member 705.

In the embodiment shown in FIG. 20A, the first member 703 comprises a base 729 configured to be affixed to the first member 106 of the knee joint and a projection 731 can extend from the base such that a tip of the projection forms the first mating portion 715 and contact the flexible tension member 719.

Figures 21, 22:
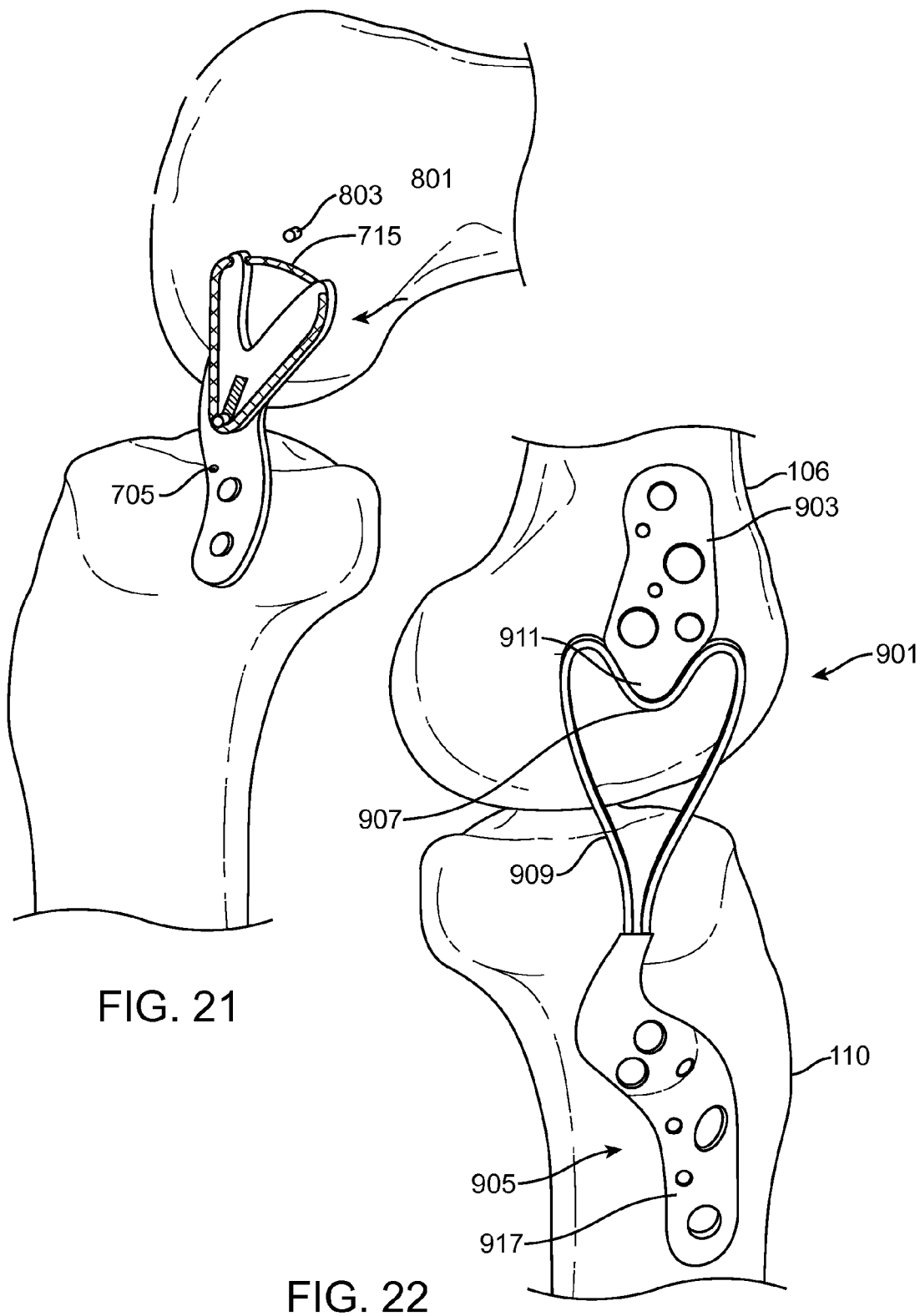
FIG. 21 is a side view of a further embodiment of an unlinked unloading device with a flexible tension member and a peg for mating with the tension member.
FIG. 22 is a side view of another embodiment of an unlinked unloading device with a Y-shaped wire spring absorber member.

An implantable knee unloading device 801 according to a further aspect of the present invention is shown in FIG. 21 and can have a first member 803 that comprises a peg 829 having a first end configured to be affixed in hole formed in the first member of the knee joint and a second end. An exterior peripheral surface of the second end of the peg 829 can form the first mating portion that can be arranged to contact a second mating portion that may be in any suitable form, such as in the form of the flexible tension member 709 as shown in FIG. 20A.

An implantable knee unloading device 901 according to another aspect of the present invention is shown in FIG. 22. The device 901 comprises a first member 903 configured to be affixed to a first member 106 of a knee joint, and a second member 905 configured to be affixed to a second member 110 of the knee joint. The second member 905 comprises a mating portion 907 comprising a resilient, flexible ring or disk 909 (hereinafter referred to as a ring). Mating portions 911 and 907 of the first and second members 903 and 905 are configured to contact one another to transmit forces between the first and second members, and the mating portions are not connected to one another. The first member 903 may be in any suitable form, such as in the form of a base with a projection 911 as shown in FIG. 22 or in the form of a peg of the type shown in FIG. 21. The second member 905 comprises a base 917 configured to be affixed to the second member 110 of the knee joint and a ring 909 forming the mating portion 907. The ring and base may be integrally formed of one-piece, such as from a NiTi material, with the ring 909 being substantially formed by a wire extending from an enlarged base portion 917 or the ring and base may be formed separately and joined together. In the illustrated embodiment, the ring 909 is adapted to be disposed outside of a capsule of the knee joint. However, the ring 909 may instead be designed to be intracapsular and positioned inside the joint space. The ring 909 can be formed so as to have a depression or concavity over an area of the exterior periphery of the ring forming the mating portion 907 of the second member 905 or it may be deformable into a concave shape upon application of a force by the mating portion 911 of the first member 903, such as when the mating portions of the first and second members contact one another to transmit ordinary forces between the first and second members. Upon application of such ordinary forces, the ring 909 will deform to absorb forces, usually by the size of the opening in center of the ring becoming larger.

Figure 23:
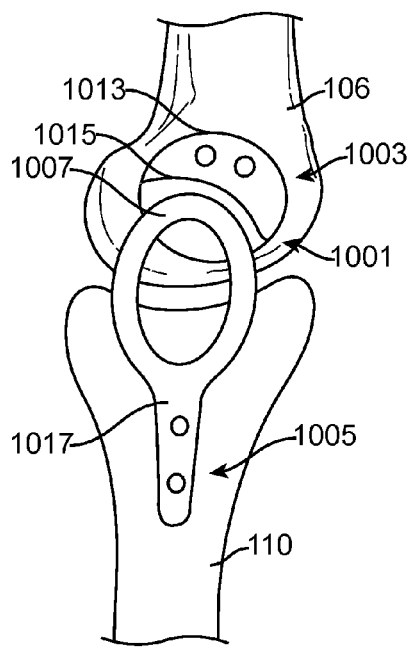
FIG. 23 is a side view of an unlinked unloading device with a flexible ring design.

In an implantable knee unloading device 1001 according to another aspect of the present invention, shown in FIG. 23, the device comprises a first member 1003 configured to be affixed to a first member 106 of a knee joint, and a second member 1005 configured to be affixed to a second member 110 of the knee joint. The second member 1005 comprises a mating portion 1007 comprising a resilient, flexible ring or disk 1009 (hereinafter referred to as a ring). Mating portions 1011 and 1007 of the first and second members 1003 and 1005 are configured to contact one another to transmit forces between the first and second members, and the mating portions are not connected to one another. The first member 1003 is in the form of a base 1013 and concave mating surface 1015 as shown in FIG. 23. The second member 1005 comprises a base 1017 configured to be affixed to the second member 110 of the knee joint. In the embodiment shown in FIG. 23, the ring and base are one-piece and may be integrally formed, such as from a NiTi material, with the ring 1009 extending from an enlarged base 1017 portion. An exterior peripheral area of the ring 1009 forming the mating portion 1007 of the second member 1005 is convex and is received in the concavity 1015 of the first member 1003, with the concavity forming the mating portion of the first member. When ordinary forces are transmitted between the first and second members, the ring 1009 can be flattened to absorb forces providing unloading of the natural knee structures.

Figure 24:
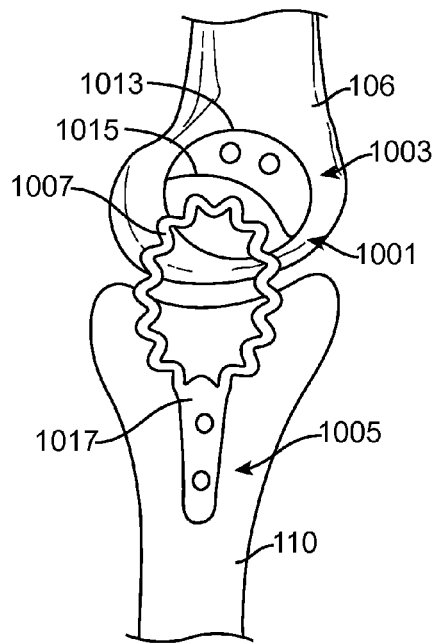
FIG. 24 is a side view of the device of FIG. 23 with a rippled ring design.

FIG. 24 shows another aspect of the implantable knee unloading device 1101 that can be substantially the same as that shown in FIG. 23, except that an exterior peripheral shape of the ring 1109 forming the mating portion 1107 of the second member 1105 ridges 1107. The ridges 1107 may be provided over the entire circumference of the ring or may be omitted in the region in which the mating portions of the first and second members contact one another to transmit forces between the first and second members. Ordinarily, the exterior peripheral shape of the ring 1109 comprises a plurality of repeating concave portions and convex portions. The ring 1109 can be compressed by flattening, as with the ring 1009 in FIGS. 23, while the arrangement and design of the ridges 1107 can be selected to adjust the force at which the ring deflects.

Figure 25:
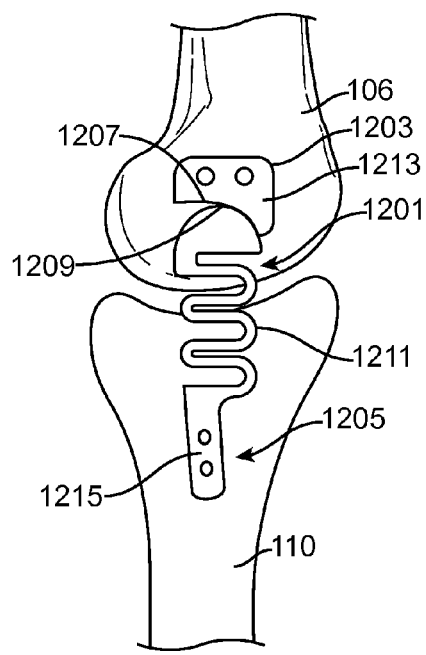
FIG. 25 is a side view of another unlinked unloading device with a contoured spring design.

FIG. 25 shows an implantable knee unloading device 1201 for a knee according to another aspect of the present invention. The device 1201 comprises a first member 1203 comprising a first base 1213 configured to be affixed to a first member 108 of a knee joint and a second member 1205 comprising a second base 1215 configured to be affixed to a second member 110 of the knee joint. First and second mating portions 1207 and 1209 of the first and second members 1203 and 1205, respectively, are configured to contact one another to transmit forces between the first and second members. The first and second mating portions 1207 and 1209 are not connected to one another. One of the first mating portion 1207 and the second mating portion 1209 comprises a concave surface and the other of the first mating portion and the second mating portion comprises a convex surface arranged to contact the concave surface to transmit forces between the first and second members. A resilient member 1211 is disposed between at least one of the first mating portion 1207 and the first base 1213 and the second mating portion 1209 and the second base 1215. The resilient member 1211 can be integrally formed with the one of the first mating portion and the first base and the second mating portion and the second base, such as in the form of a spring member 1211 as shown in FIG. 25. The spring member 1277 as shown in FIG. 25 is a low profile wave spring, however other spring configurations may also be used.

FIG. 26 shows an implantable knee unloading device 1301 for a knee according to another aspect of the present invention. The device 1301 comprises a first member 1303 comprising a first base 1313 configured to be affixed to a first member 106 of a knee joint and a second member 1305 comprising a second base 1315 configured to be affixed to a second member 110 of the knee joint. First and second mating portions 1307 and 1309 of the first and second members 1303 and 1305, respectively, are configured to contact one another to transmit forces between the first and second members. The first and second mating portions 1307 and 1309 are not connected to one another. The first mating portion 1307 and the second mating portion 1309 both comprise convex surfaces arranged to contact each another to transmit ordinary forces between the first and second members. A resilient member 1311a and 1311b is disposed between at least one of, and ordinarily both of, the first mating portion 1307 and the first base 1313 and the second mating portion 1309 and the second base 1315. The resilient member 1311a and 1311b can be a resilient, compressible material as shown in FIG. 26. Resilient materials suitable for the members 1311a and 1311b include materials approved for and suitable for use in the human body, such as silicon.

An implantable knee unloading device 1401 for a knee according to another aspect of the present invention is shown in FIG. 27 and comprises a first member 1403 comprising a first base 1413 configured to be affixed to a first member 106 of a knee joint and a second member 1405 comprising a second base 1415 configured to be affixed to a second member 110 of the knee joint. First and second mating portions 1407 and 1409 of the first and second members 1403 and 1405, respectively, are configured to contact one another to transmit forces between the first and second members. The first and second mating portions 1407 and 1409 are not connected to one another. The first mating portion 1407 is in the form of a cam surface and the second mating portion 1409 is in the form of a cam follower. The cam surface 1407 is concavely curved in the medial lateral direction to form a track along which the follower 1409 can ride without disengaging. The cam surface 1407 is convexly curved in the anterior posterior direction with a curvature of the cam surface in this direction designed to provided unloading of the joint a desired portions of the gait cycle. The cam surface 1407 of the first mating portion 1407 can be shaped to maintain a substantially constant distance between reference points on the first and second members 108 and 110 of the knee joint when the cam surface is contacted by the second mating portion if continuous unloading throughout the gait cycle is desired. The second mating portion 1409 in the form of the cam follower can be in any suitable form, such as one of a rolling cylindrical head, a rolling ball head, and a solid sliding head for contacting the first mating portion 1407.

The second mating portion 1409 is in the form of a sliding piston which slides within an arbor 1411 containing a biasing spring. The spring can be designed to keep the piston 1409 in continuous contact with the cam surface 1407 or can allow the follower to disengage from the cam surface 1407 when the device is not active, such as when the knee joint is flexed at 90 degrees.

An implantable knee unloading device 1501 for a knee according to another aspect of the present invention is shown in FIG. 28 and comprises a first member 1503 comprising a first base 1513 configured to be affixed to a first member 108 of a knee joint and a second member 1505 comprising a second base 1515 configured to be affixed to a second member 110 of the knee joint. First and second mating portions 1507 and 1509 of the first and second members 1503 and 1505, respectively, are configured to contact one another to transmit forces between the first and second members. The first and second mating portions 1507 and 1509 are not connected to one another. The first mating portion 1507 comprises a beam 1507 that is arranged to extend generally in the anterior posterior direction relative to the first member 106 of the knee joint. The second mating portion 1509 comprises an abutment surface 1509 arranged to contact the beam. The beam 1507 is adapted to deflect as a spring beam when the mating portions of the first and second members 1503 and 1505 contact one another to transmit forces between the first and second members. The shape of the spring beam 1507 and the location of the contact point between the mating members can be configured to achieve unloading of the knee joint as desired for a particular patient or a particular condition.

Figures 29, 30A:
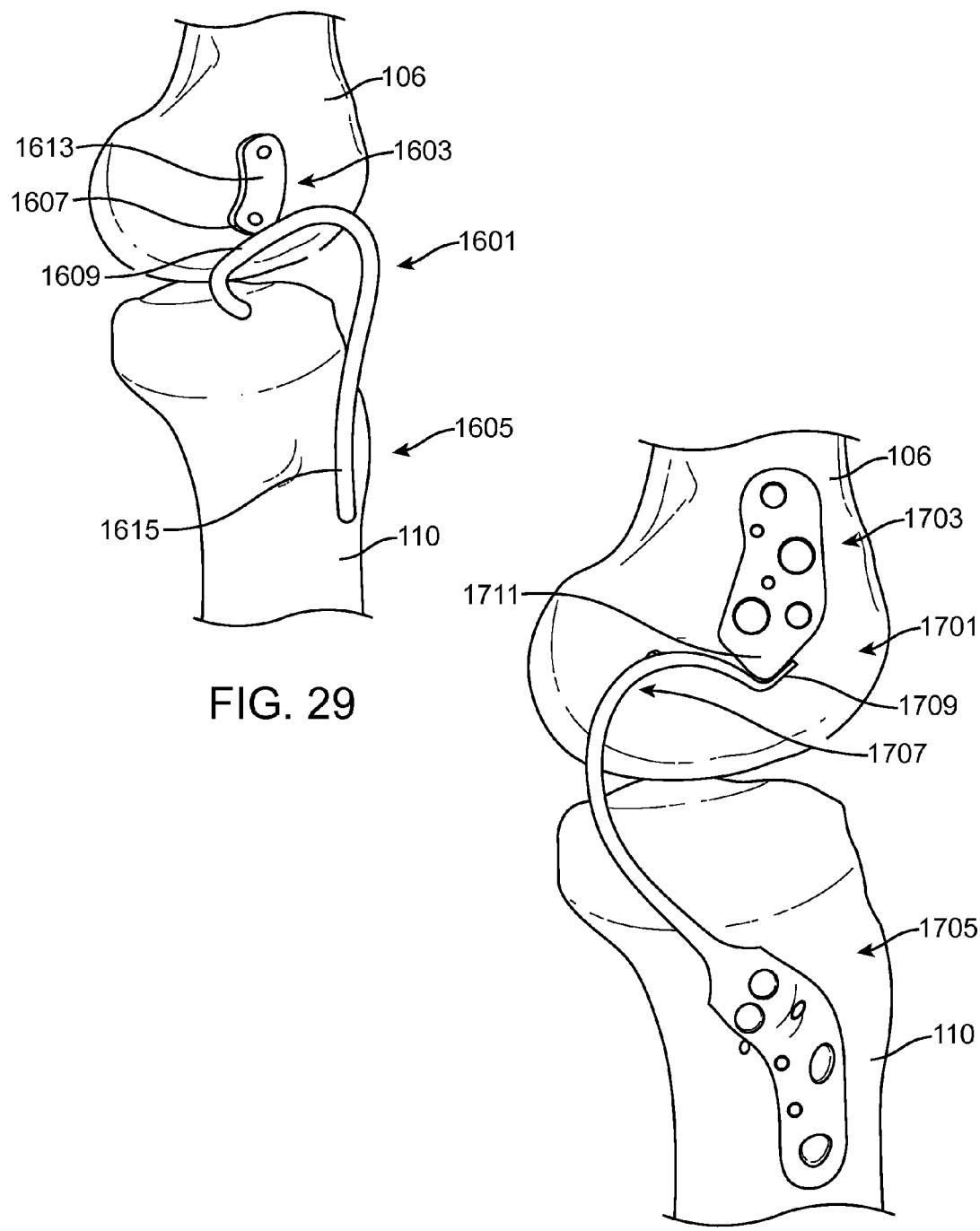
FIG. 29 is a side view of another spring beam version of an unlinked unloading device.
FIG. 30A is a side view of a further spring beam version of an unlinked unloading device.

An implantable knee unloading device 1601 for a knee according to another aspect of the present invention is shown in FIG. 29 and is essentially an inverted version of the device 1501 of FIG. 28. It should be understood that the other embodiments of unloading devices described herein can also be inverted from the arrangements shown and still achieve unloading of the joint.

The knee unloading device 1601 of FIG. 29 comprises a first member 1603 comprising a first base 1613 configured to be affixed to a first member 106 of a knee joint and a second member 1605 comprising a second base 1615 configured to be affixed to a second member 110 of the knee joint. First and second mating portions 1607 and 1609 of the first and second members 1603 and 1605, respectively, are configured to contact one another to transmit forces between the first and second members. The first and second mating portions 1607 and 1609 are not connected to one another. The second mating portion 1609 comprises a spring beam 1609 that is arranged to extend generally alongside the second member 110 of the knee joint and extends in an anterior posterior direction. The first mating portion 1607 comprises an abutment surface arranged to contact the beam. The beam 1609 is adapted to deflect through an angle of sufficient to provide unloading of about 10-50 pounds of weight from the natural joint when the mating portions 1607 and 1609 of the first and second members 1603 and 1605 contact one another to transmit ordinary forces between the first and second members.

Figure 30C:
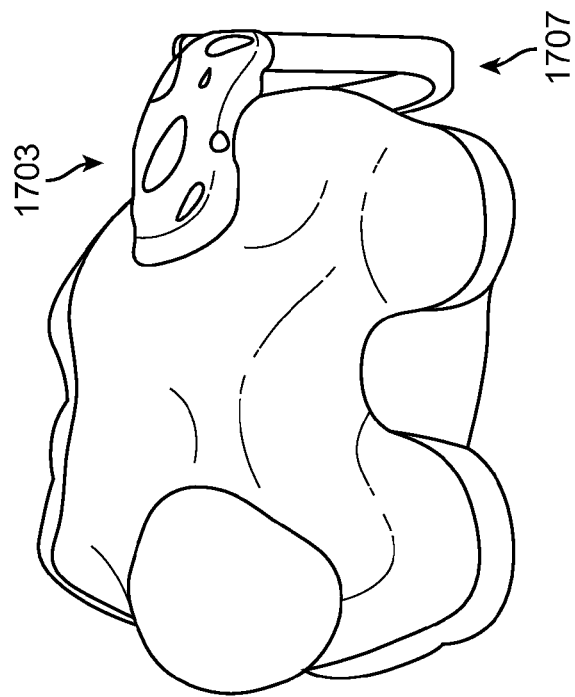
FIG. 30C is a top view of the device of FIG. 30A.
Figure 30B:
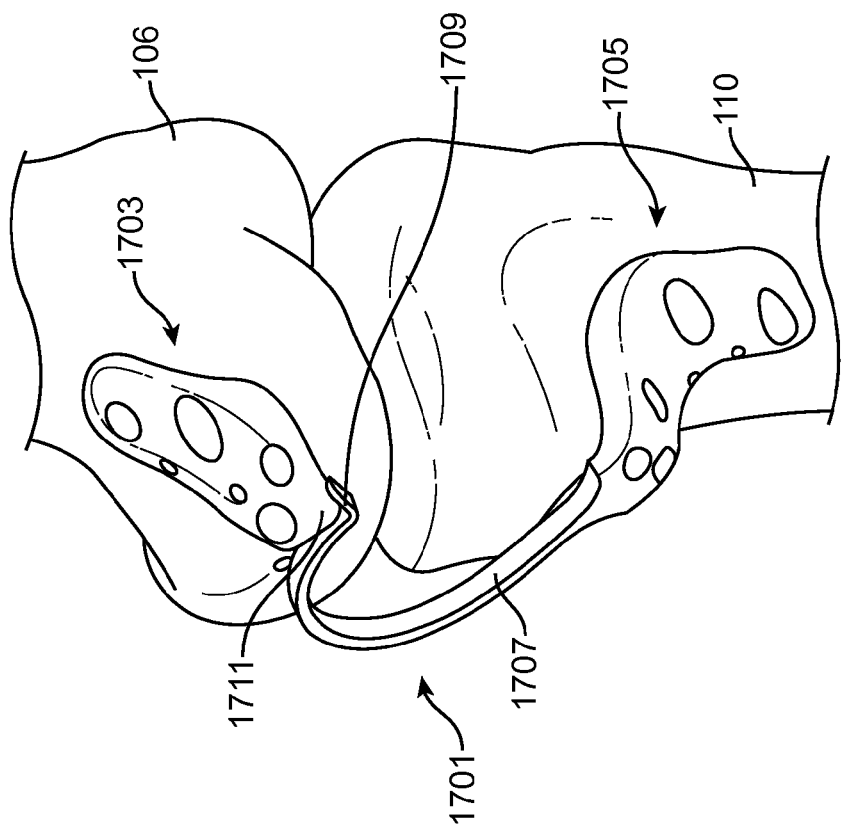
FIG. 30B is a perspective view of the device of FIG. 30A.
Figure 30D:
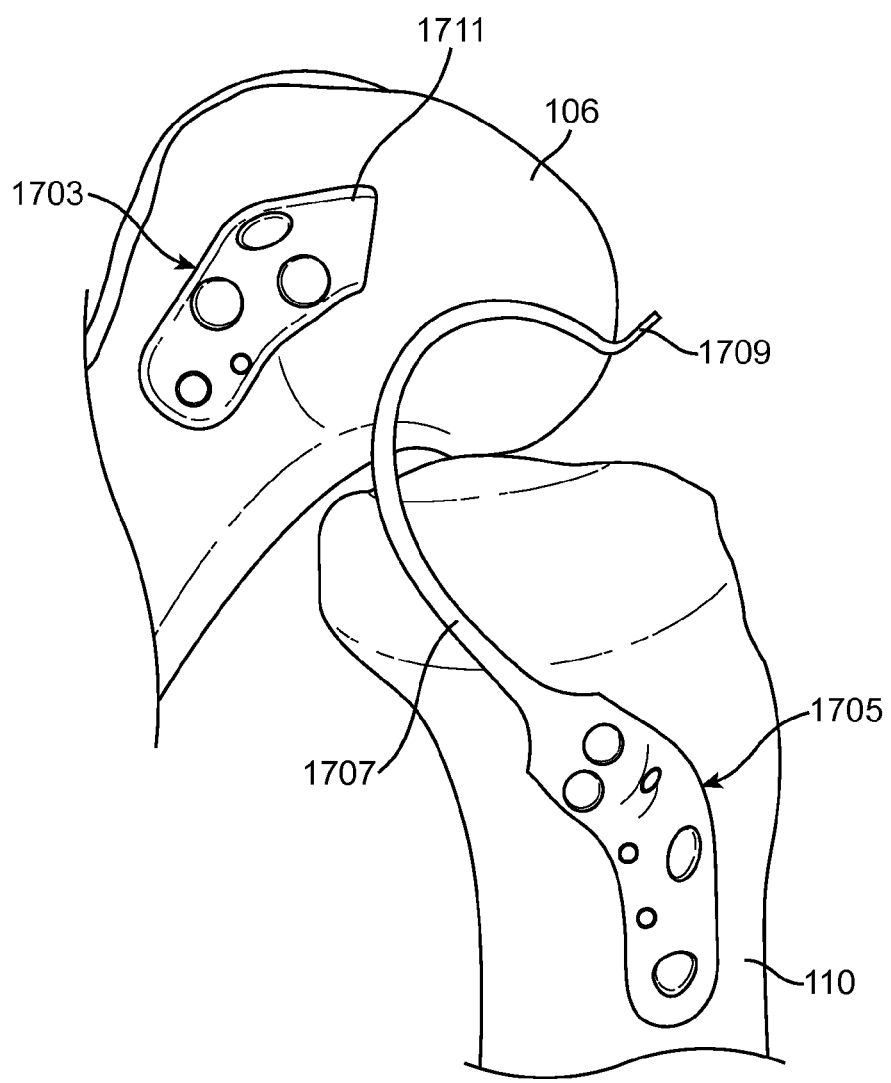
FIG. 30D is a side view of the device of FIG. 30A with the knee joint shown in flexion.

FIGS. 30A-D show a joint unloading device 1701 having a first member 1703 and a second member 1705 formed with a leaf spring or beam spring 1707 similar to those embodiments of FIGS. The spring 1707 is a C shaped spring having an upper notched end 1709 configured to receive a projection 1711 of the first member. The C shaped spring 1707 can be contoured to provide a desired unloading profile for the joint. The unloading device 1701 as shown provides unloading of the joint when the knee joint is in extension and provides no joint unloading beyond about 20 degrees of flexion (FIG. 30D).

Although actual springs are used to show various embodiments herein, these spring elements could also be substituted with a material or other device with spring-like characteristics (e.g., an elastomeric member). Such elastomers include thermoplastic polyurethanes such as Tecoflex, Tecothane, Tecoplast, Carbothene, Chronthane and ChronoFlex (grades AR, C, AL) which also could be employed as a dampener. Moreover, materials such as Pebax, C-flex, Pellathane, silicone and silicone foam can also be employed.

A 5 to 20% energy or load reduction has been postulated to be desirable in certain circumstances to accomplish the alleviation of pain without approaching undesirable load shielding.

As mentioned above, the present invention has applications to various parts of the body. For example, an energy manipulation assembly can be placed within the cavity between the acromiom and the humerus bones. An energy manipulation assembly can also be placed between the tibia and the calcareous bones to address problems with the ankle Such an approach can help alleviate pain as well as address symptoms associated with a condition referred to as drop foot. Thus, the assembly can be configured to accomplish a lifting motion on the foot.

Moreover, applications to the hand and finger are also contemplated. Here, one or more load manipulating assemblies can be positioned between distal and middle phalanges as well as between middle and proximal phalanges. Moreover, distraction units can be placed between adjacent phalanges to treat various conditions. Additionally, a load sharing or energy manipulating device can be attached to and placed between vertebra to off-load a disc. The energy manipulation device can be attached to the side of the vertebra or can be affixed to facets.

It is to be borne in mind that each of the disclosed various structures can be interchangeable with or substituted for other structures. Thus, aspects of each of the bending spring, cam engagement, segmented support and piston support assemblies can be employed across approaches. Moreover, the various manners of engaging energy absorbing structure with attachment structure and attachment structures to body anatomy can be utilized in each approach. Also, one or more of the various disclosed assemblies can be placed near a treatment site and at various angles with respect thereto. Pressure sensing and drug delivery approaches can also be implemented in each of the various disclosed embodiments.

Certain members of most embodiments of the present invention can be made in multiple parts designed for modular assembly of different sizes and shapes and for easy removal and, if necessary replacement of some members or parts of members without removal of the entire system. The permanent parts include fixation components which have bony ingrowth promoting surfaces and are responsible for fixation of the system to the skeletal structure. The removable parts can include the mobile elements of the system.

The advantages of this feature of the system include the ability to exchange some parts of the system due to unanticipated wear, patient condition change or newer improved systems being available. Additionally if the patient subsequently requires further surgery the entire implantable unloading device may be removed to facilitate the additional procedure.

Further, certain of the contemplated mechanisms can be made to be completely disengaged mechanically and then be brought into action under various conditions and during certain phases of the gait cycle. This discontinuous functionality—and the ability to tune that functionality to a particular patient's gait or pain is consequently a feature of the present invention. For example, by selection from a variety of different available lengths of first or second members, the unloading can be tailored to a particular portion of the gait cycle. In one embodiment, the first and second members are configured to engage one another to absorb at least a portion of the total load applied to the knee during at least 5 degrees and during no more than 60 degrees of a natural range of motion of the knee.

Location of the permanent fixation components is important to fixation strength, ability to complete subsequent procedures, and location of pivots or other joints. The fixation strength of the system, and therefore load bearing capacity, is dependent on the integrity of the bone onto which the member is fixed. To ensure strong fixation, in one embodiment, the fixation components span along the cortical bone and cancellous (or trabecular) bone. For example on the knee, the member would reside on the femoral shaft and extend down onto the trabecular bone on the end of the femur. Also, the system may utilize fixation on two cortical surfaces using through pins or bicortical screws.

A common joint procedure is joint replacement as previously described. The procedure of replacing a diseased joint includes resection of the surfaces of the joint and replacement with synthetic materials. To enable implantation of the energy absorbing system or knee unloading device without impacting the potential to complete subsequent procedures (e.g., joint replacement) the permanent fixation components in a preferred embodiment are positioned at a location that does not compromise the total joint zone. In other words, in a preferred embodiment, the entire joint unloading system is extra-articular and entirely outside the joint capsule.

Many articulating joints are not simply pivot joints but involve complex multi-axis rotation and translation movements. To achieve its intended purpose, the unloading device should accommodate these movements but also absorb and transfer energy during the required range of motion. To do so the device should be located at points on the bones selected to achieve the desired motion. The device joint locations may be finely adjusted within a defined region on the fixation component to further optimize the device joint location. In addition, the unloading device may include one or more movable joint mechanisms (such as a universal joint) which accommodates the positional changes and therefore can increase the flexibility of fixation location for the members.

The forces on the knee joint change throughout the gait cycle. However, in body anatomy incorporating the present invention, the unloading forces counteract the normal force on the knee joint during certain portions of the gait cycle. Where the body joint is treated with the foregoing described unloading assemblies of the present invention, a part of the forces between on the joint are absorbed by the unloading device, reducing the overall forces on the joint during certain portions of the gait cycle. Accordingly, less force is placed on the natural joint anatomy.

Figure 31:
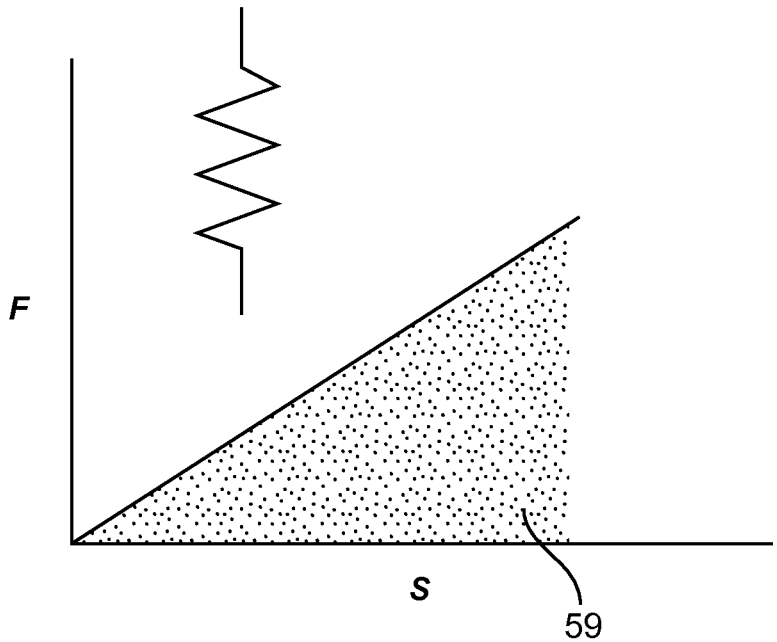
FIG. 31 is a graph, illustrating the energy characteristics of a linear spring system of the present invention.
Figure 32:
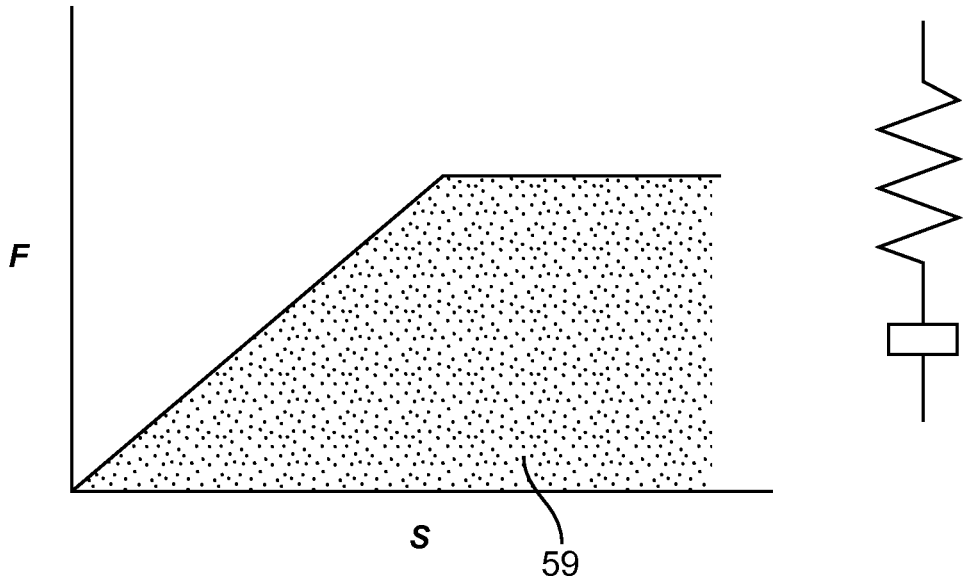
FIG. 32 is a graph, illustrating the energy characteristics of a spring and dampening system of the present invention.

FIGS. 31-32 depict the relation between force (F) and displacement (S) between members of a body joint (where mass is constant). In an energy manipulating or unloading system incorporating a single linear spring (FIG. 31), energy is absorbed in proportion to a spring constant (spring stiffness). The energy absorbed is represented by the shaded area 59 below the curve. As shown in FIG. 32, where a spring and dampener are used in combination, the energy absorbed 59 is a function of the spring constant and the dampener. It is these relationships which are used in developing desired energy manipulating characteristics.

Figure 33:
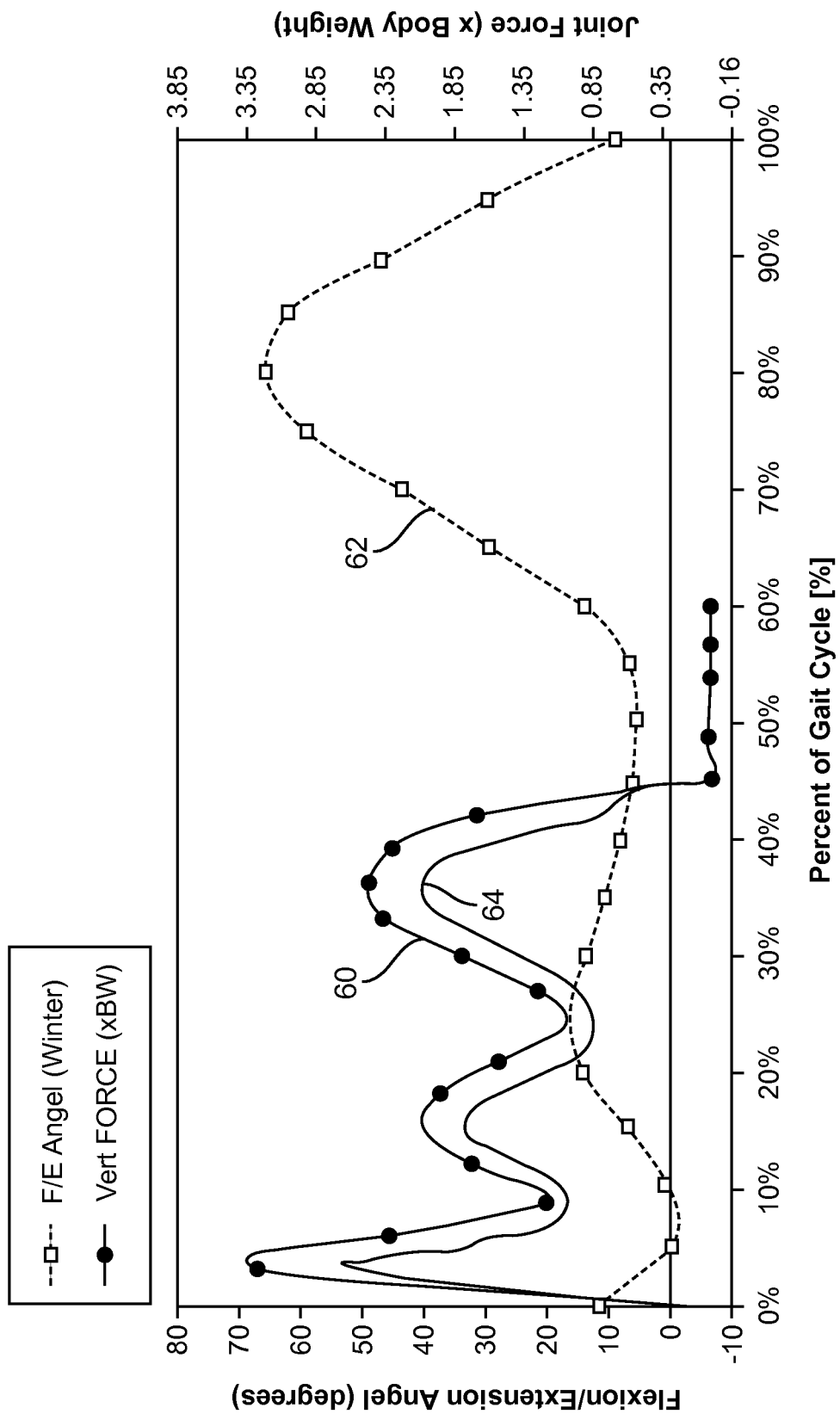
FIG. 33 is a graph, illustrating the flexion/extension angle and joint force existing in a gait cycle and illustrating one approach to energy absorption on a gait cycle.

Also considered are the forces existing through flexion and extension during an articulation cycle of anatomy to be treated. Using the gait cycle of the legs of a human as an example, both the joint force and flexion/extension angle in degrees can be plotted versus the percentage of the gait cycle completed. A normal or expected relationship 60 of vertical forces generated through the gait cycle is depicted in each of FIG. 33. Also depicted in FIG. 33 is the flexion/extension angle 62. The expected relationship 60 of vertical forces during the gait cycle can be altered using certain of the embodiments of the joint unloading devices of the present invention. As shown in FIG. 33, the unloading device can absorb energy by a fixed proportion during a portion of the gait cycle. This is reflected by the curve 64. Moreover, energy can be both absorbed and dampened or alternatively, energy can be absorbed only above a fixed value. Additionally, energy can be absorbed in a fixed range of motion. It is to be recognized, however, that each of or one or more of these types of energy absorption can be combined in a desired system.

With the anatomy of the knee joint in mind, a pre-operative session with the patient is conducted. By employing two-dimensional or three dimensional static or motion imaging techniques which are available, such as x-ray, MRI or CT scans, the anatomy of the interventional site is examined. A dynamic assessment can be performed to map the articulating motion of the members defining the particular joint. In a procedure seeking to off-load or manipulate forces at a knee joint, a proximal (femoral) attachment site for a first member 104 of an unloading device must be identified. Similarly, a distal (tibial) attachment site must also be selected for attachment of the second member 108. In a contemplated approach the medial proximal attachment site can be located on a femur in a space bounded by the medial patellar retinaculum, the vastus medialis and the tibial collateral ligament. The distal attachment site can be located on the tibia in a space between the medical patellar retinaculum and the pes anserinus.

The data collected during the pre-operative session is logged and then compared to data sets developed by the physician and/or the organization utilized to store actual patient data as well as tested theoretical data independently developed. Easily accessible and convenient to use programs or charts can be developed and employed to automate the comparison of a particular patient's condition with previously collected data. From this comparison, a specific treatment modality is selected for the patient. Moreover, an expected device selection or multiple device selections are made from the various devices contemplated to treat the patient.

One example of a method for implantation of the unloading devices described herein, spinal anesthesia or general anesthesia can be used. Next, the knee or other joint being treated is imaged using fluoroscopy and/or three-dimensional navigational software such as that available from Striker or Brainlab. The members defining the joint are placed in a full lateral position and perpendicularly to the receiver of the imaging device. The proximal joint member is then fixed using a vacuum splint/sandbag (not shown) or similarly effective device. In a preferred procedure to treat the knee joint, the Blumensaat's line of the femur bone is used as a landmark for locating the various components of an unloading device as it has been found to provide a convenient initial position marker for ultimately achieving proper rotational positioning of the device. Other referencing points can additionally be used and of course are required when treating other joints.

Accordingly, it is further contemplated that other regions can represent possible locations of a femoral rotation point or reference point on the medial chondyle. In order to select such an alternative point, the surface area of the medial chondyle is mapped to determine regions corresponding to changes in spacing distance between potentially implanted first and second members while the joint is moved from full extension to full flexion. This information is then employed to identify the various points of attachment best suited for a particular unloading device. This information is also employed to identify the size and/or shape of the first and second members to be implanted.

In a contemplated approach, a first member is attached to the femur and a second member is attached to the tibia. Energy absorbing surfaces are provided at a junction between the members. The surfaces allow multiple degrees of freedom between the first and second members. A subcutaneous tissue barrier in the form of a sheath, preferably ePTFE, which encloses various parts of the system and excludes surrounding tissue can be further provided. It is contemplated that the subcutaneous tissue barrier can be formed from or coated alternatively with a tissue in-growth substance or for that matter, substances which inhibit such in-growth. For example, the sheath or tissue barrier can surround both of the terminal ends 130, 140 of the first and second members to prevent tissue impingement between the terminal ends.

Therefore, the unloading device of the present invention provides a number of ways to treat body tissues and in particular, to absorb energy or manipulate forces to reduce pain. The present invention can be used throughout the body but has clear applications to articulating body structures such as joints.

Thus, it will be apparent from the foregoing that, while particular forms of the invention have been illustrated and described, various modifications can be made without parting from the spirit and scope of the invention.

We claim:

1. An implantable knee unloading device for a knee comprising:
    a first member configured to be affixed to a first member of a knee joint;
    a second member configured to be affixed to a second member of the knee joint;
    mating portions of the first and second members configured to contact one another to transmit force between the first and second members, wherein the mating portions are not connected to one another; and
    wherein the knee unloading device is configured to be implanted outside of the joint capsule and to absorb at least a portion of the total load applied to the knee during at least 5 degrees and during no more than 90 degrees of a natural range of motion of the knee.

2. The device of claim 1, wherein the first member comprises an energy absorber.

3. The device of claim 2, wherein the energy absorber comprises a piston, sleeve and spring assembly.

4. The device of claim 1, further comprising a biasing member configured to adjust a length of at least one of the first and second members, the biasing member configured to maintain the mating portions of the first and second members in contact with each other throughout the natural range of motion of the knee.

5. The device of claim 1, wherein the entire knee unloading device is configured to be implanted entirely outside of the articulating surfaces of the knee.

6. The device of claim 1, wherein the mating portions of the first and second members are in contact with one another during only a portion of the natural range of motion of the knee joint, and wherein the portion includes full extension of the knee joint.

* * * * *